United States Patent
Gahler et al.

(10) Patent No.: US 11,980,214 B2
(45) Date of Patent: May 14, 2024

(54) DIETARY FIBER COMPOSITIONS WITH PSYLLIUM AND METHODS OF USE

(71) Applicant: InovoBiologic Inc., Calgary (CA)

(72) Inventors: Roland Jacques Gahler, Burnaby (CA); Simon Wood, Victoria (CA)

(73) Assignee: InovoBiologic Inc., Calgary (CA)

( * ) Notice: Subject to any disclaimer, the term of this patent is extended or adjusted under 35 U.S.C. 154(b) by 0 days.

(21) Appl. No.: 17/776,539

(22) PCT Filed: Nov. 12, 2020

(86) PCT No.: PCT/CA2020/051540
§ 371 (c)(1),
(2) Date: May 12, 2022

(87) PCT Pub. No.: WO2021/092691
PCT Pub. Date: May 20, 2021

(65) Prior Publication Data
US 2022/0346428 A1   Nov. 3, 2022

Related U.S. Application Data

(60) Provisional application No. 62/936,057, filed on Nov. 15, 2019.

(51) Int. Cl.
| | | |
|---|---|---|
| A61K 36/00 | (2006.01) | |
| A23L 29/244 | (2016.01) | |
| A23L 29/256 | (2016.01) | |
| A23L 29/269 | (2016.01) | |
| A23L 33/22 | (2016.01) | |
| A61P 3/04 | (2006.01) | |

(52) U.S. Cl.
CPC ............. *A23L 33/22* (2016.08); *A23L 29/244* (2016.08); *A23L 29/256* (2016.08); *A23L 29/27* (2016.08); *A61P 3/04* (2018.01)

(58) Field of Classification Search
CPC ..... A61K 36/68; A61K 31/736; A61K 31/734
See application file for complete search history.

(56) References Cited

U.S. PATENT DOCUMENTS

| | | |
|---|---|---|
| 8,003,152 B1 | 8/2011 | Xiong et al. |
| 2006/0228397 A1 | 10/2006 | Gahler et al. |
| 2011/0117622 A1* | 5/2011 | Yoshikado ........... A61K 9/4891 435/180 |

FOREIGN PATENT DOCUMENTS

| | | |
|---|---|---|
| CA | 2 665 888 A1 | 4/2008 |
| EP | 1 887 891 B1 | 9/2014 |

OTHER PUBLICATIONS

Pizzorno et al. ("Diabetes Mellitus" from The Clinician's Handbook of Natural Medicine. 2016. Elsevier, Inc: Missouri. p. 277). (Year: 2016) (Year: 2016).*
International Search Report dated Jan. 26, 2021, issued in corresponding International Patent Application No. PCT/CA2020/051540, filed Nov. 12, 2020, 6 pages.
Written Opinion dated Jan. 26, 2021, issued in corresponding International Patent Application No. PCT/CA2020/051540, filed Nov. 12, 2020, 5 pages.
Kristensen, M., et al., "Dietary Fibres in the Regulation of Appetite and Food Intake. Importance of Viscosity," Appetite 56(1):65-70, Feb. 2011.
Smith, I.H., et al., "Viscosity Development During Aqueous Dispersion and Dissolution: A Comparison of PGX® with Other Dietary Supplements and Individual Polysaccharides," Food Hydrocolloids 38:152-162, 2014.
Jane, M., et al., "Effects of Daily Consumption of Psyllium, Oat Bran and polyGlycopleX on Obesity-Related Disease Risk Factors: A Critical Review," Nutrition 57:84-91, 2019.
Extended European Search Report dated May 26, 2023, issued in correponding European Patent Application No. 20887639.1, filed Nov. 12, 2020, 13 pages.
Mintel Global New Products Database, Anonymous: "Sugar-Free Thin Noodles", <https://www.gnpd.com>, XP93045050, Database Accession No. 6667389, Jun. 26, 2019, 2 pages.
Pal S., et al., "Effect on Insulin, Glucose and Lipids in Overweight/Obese Australian Adults of 12 Months Consumption of Two Different Fibre Supplements in a Randomised Trial", Nutrients 9(2):91, Jan. 29, 2017, 13 pages.

* cited by examiner

*Primary Examiner* — Qiuwen Mi
(74) *Attorney, Agent, or Firm* — Christensen O'Connor Johnson Kindness PLLC

(57) ABSTRACT

A dietary composition comprising (i) from about 40% to about 80% (w/w) of a fiber composition comprising glucomannan, xanthan gum, and alginate; and (ii) from about 10% to about 60% (w/w) psyllium is provided, along with a method and a food product for promoting satiety, promoting weight loss, lowering blood cholesterol levels or lowering blood glucose levels in a mammal.

12 Claims, 11 Drawing Sheets

DIETARY FIBER COMPOSITIONS WITH PSYLLIUM AND METHODS OF USE

FIELD OF THE INVENTION

The invention relates to dietary fiber compositions and their use to suppress appetite, promote weight loss, lower blood cholesterol levels and lower blood glucose levels.

BACKGROUND

Dietary fiber recommendations for adults in the United States, Canada and Australia are 25-30 grams per day to be consumed from fiber-rich foods (Marlett et al., *J. Am. Diet. Assoc.* 2002; 102:993-1000). However, it is estimated that adults in these countries consume only about 15-25 grams of dietary fiber per day (U.S. Department of Agriculture and U.S. Department of Health and Human Services, Dietary Guidelines for Americans, Washington: U.S. Gov. Printing Office, 2005; National Health and Medical Research Council, Australian Dietary Guidelines. Canberra: National Health and Medical Research Council; 2013). Epidemiological and cohort studies have consistently revealed that higher fiber intakes are correlated with lower body weight, body mass index (BMI) and waist circumference (Du et al., *Am. J. Clin. Nutr.* 2010; 91:329-36; Newby et al., *Am. J. Clin. Nutr.* 2007; 86:1745-53), improved lipid profiles (Wu et al., *Am. J. Clin. Nutr.* 2003; 78:1085-91; Lairon, *Atheroscler Suppl.* 2008; 9:45-8; Kan et al., *Am. J. Clin. Nutr.* 2007; 86:1626-32; Lairon et al., *Am. J. Clin. Nutr.* 2005; 82:1185-94; Venn and Mann, *Eur. J. Clin. Nutr.* 2004; 58:1443-61; Weickert and Pfeiffer, *J. Nutr.* 2008; 138:439-42; McKeown et al., *Am. J Clin. Nutr.* 2002; 76:390-8; Brown et al., *Am. J Clin. Nutr.* 1999; 69:30-42; Pittler and Ernst, *Am. J Med.* 2001; 110:724-30), glycemia and insulinemia (Ludwig et al., *JAMA* 1999; 282:1539-46), indicating the benefits and risk reduction for metabolic syndrome, cardiovascular disease and type 2 diabetes.

Although the benefits of fiber are well known, people typically find it difficult to consume the required amounts of fiber by increasing fruit and vegetable intake (Clemens et al., *J Nutr.* 2012; 142:13905-4015). Thus, there is a need for dietary fiber compositions that provide an easy, cost effective method for increasing fiber intake without the need for other major dietary modifications and assist in promoting satiety, promoting weight loss, lowering blood cholesterol levels and lowering blood glucose levels. The present invention addresses these needs and others.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the invention provides a dietary composition comprising (i) from about 40% to about 80% (w/w) of a fiber composition comprising glucomannan, xanthan gum, and alginate; and (ii) from about 10% to about 60% (w/w) psyllium. In one embodiment, the dietary composition comprises from about 50% to about 60% (w/w) of the fiber composition and from about 40% to about 50% (w/w) psyllium.

In one embodiment, the fiber composition comprises from about 50% to about 90% (w/w) glucomannan, from about 5% to about 20% (w/w) xanthan gum, and from about 5% to about 30% (w/w) alginate. In one embodiment, the fiber composition comprises from about 60% to about 80% (w/w) glucomannan, from about 10% to about 20% (w/w) xanthan gum, and from about 10% to about 20% (w/w) alginate. In one embodiment, the fiber composition is granulated. In one embodiment, the fiber composition and psyllium are granulated.

In one embodiment, the dietary composition includes at least one lipid or blend thereof, wherein the lipid or blend thereof comprises at least 20% (w/w) of the total fiber composition. In one embodiment, the dietary composition is contained in a soft gel capsule, compounded into a tablet, or formulated into a powder.

In another aspect, the present invention provides a method for promoting satiety, promoting weight loss, lowering blood cholesterol levels or lowering blood glucose levels in a mammal, comprising administering to a mammal a dietary composition comprising (i) from about 40% to about 80% (w/w) of a fiber composition comprising glucomannan, xanthan gum, and alginate; and (ii) from about 10% to about 60% (w/w) psyllium, in an amount effective to promote satiety, promote weight loss, or lower blood glucose levels.

In one embodiment, the fiber composition comprises from about 50% to about 90% (w/w) glucomannan, from about 5% to about 20% (w/w) xanthan gum, and from about 5% to about 30% (w/w) alginate. In one embodiment, the fiber composition is granulated. In one embodiment, the fiber composition and psyllium are granulated.

In one embodiment, the fiber composition includes at least one lipid or blend thereof, wherein the lipid or blend thereof comprises at least 20% (w/w) of the total fiber composition. In one embodiment, the dietary composition is contained in a soft gel capsule, compounded into a tablet, or formulated into a powder.

In another aspect, the present invention provides a food product for promoting satiety, promoting weight loss, lowering blood cholesterol levels or lowering blood glucose levels in a mammal comprising a dietary composition comprising (i) from about 40% to about 80% (w/w) of a fiber composition comprising glucomannan, xanthan gum, and alginate; and (ii) from about 10% to about 60% (w/w) psyllium.

In one embodiment, the fiber composition comprises from about 50% to about 90% (w/w) glucomannan, from about 5% to about 20% (w/w) xanthan gum, and from about 5% to about 30% (w/w) alginate. In one embodiment, the fiber composition is granulated. In one embodiment, the fiber composition and psyllium are granulated.

In one embodiment, the food product is a dietary supplement or a meal replacement product. In one embodiment, the food product is compounded to provide a daily dose of from about 5 grams to about 20 grams of the dietary composition.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
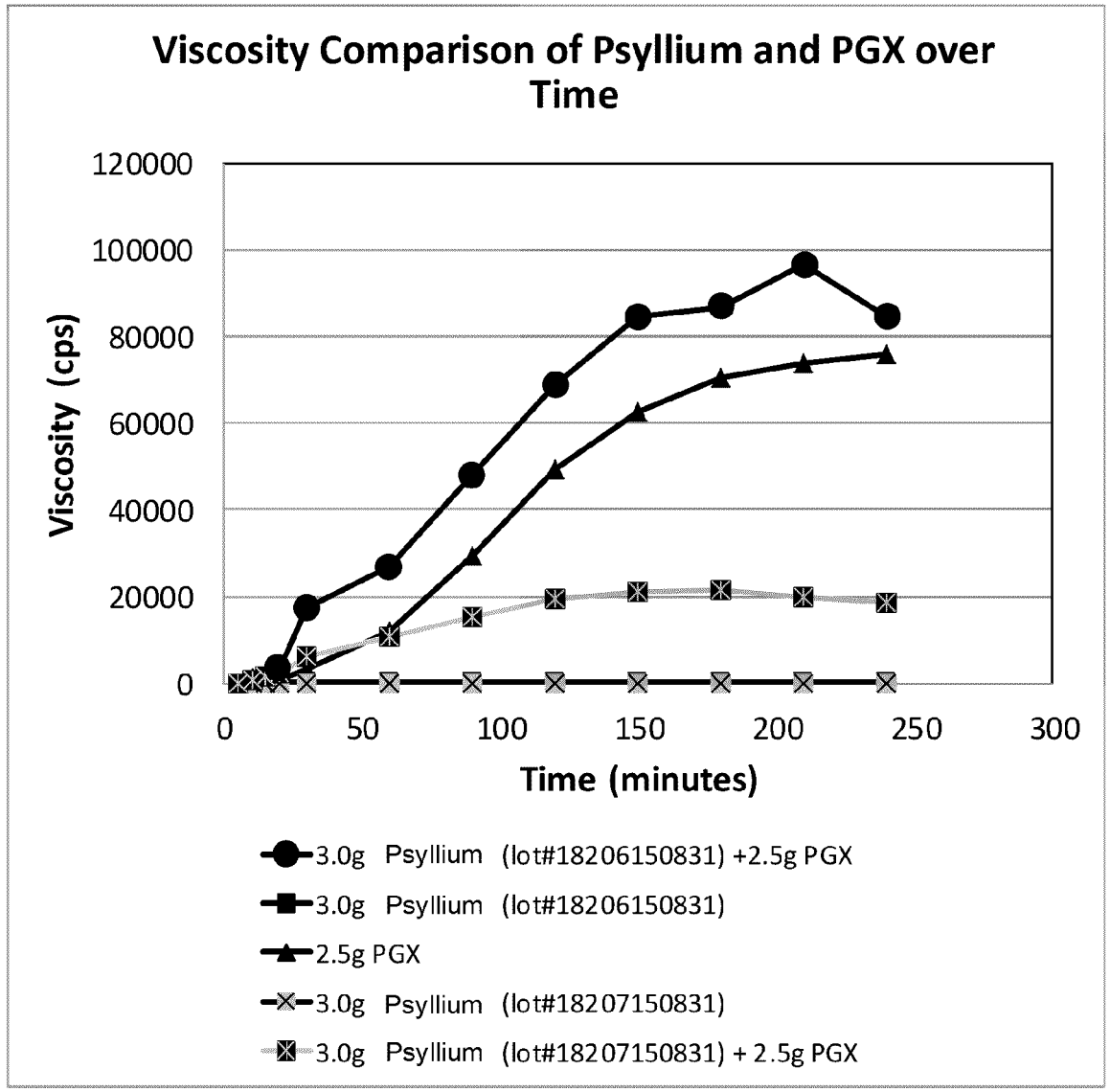
FIG. 1 graphically illustrates the viscosity profiles of representative compositions comprising PGX®, psyllium and a combination of PGX and psyllium.

The proprietary fiber composition POLYGLYCOPLEX®, also known as PGX, (InovoBiologic Inc., Calgary, Alberta, Canada) is a highly viscous functional non-starch polysaccharide complex that exhibits developing viscosity in water and under gastric conditions and is manufactured using a proprietary process called EnviroSimplex® from konjac (glucomannan), sodium alginate and xanthan gum. Adding 2.5-5 grams of PGX to a meal is highly effective in reducing postprandial glycemia, lowering the glycemic index of food (Jenkins et al., *Nutr. J.* 2010; 9:58) and modifying satiety hormones in healthy adults (Reimer et al., *Eur. J. Clin. Nutr.* 2010; 64:1186-91). As used herein, the term "fiber composition" can include, for example, a granulated fiber composition or a non-granulated fiber composition. The term "PGX" can include, for example, granulated PGX or non-granulated PGX. Granulation is described in more detail below.

Psyllium is a soluble fiber derived from members of the plant genus *Plantago*. Commonly used as a fiber supplement, psyllium is available in several flavors sold as powdered drink mixes, capsules or wafers. Psyllium is not absorbed by the small intestine and typically absorbs excess water while stimulating normal bowel movements. Psyllium has certain advantages over other types of soluble fiber; because it is less readily fermented, psyllium causes less flatulence and abdominal bloating (Blackwood et al., *J. R. Soc. Promot. Health.* 2000; 120:242-7). *Psyllium* has been evaluated in various human studies for beneficial effects on glucose and insulin homeostasis, lipids and lipoprotein, body weight, body composition and appetite (Pal et al., *Br. J. Nutr.* 2011; 105:90-100; Ziai et al., *J. Ethnopharmacol.* 2005; 102:202-7; Karhunen et al., *J. Nutr.* 2010; 140:737-44; Anderson et al., *Am. J. Clin. Nutr.* 2000; 71:472-9; Rodriguez-Moran et al., *J. Diabetes Complications* 1998; 12:273-8; Vuksan et al., *Br. J. Nutr.* 2011; 106:1349-52; Tai et al., *Ann. Acad. Med. Singapore* 1999; 28:209-13; Turnbull and Thomas, *Int. J. Obes. Relat. Metab. Disord.* 1995; 19:338-42; Delargy et al., *Int. J. Food Sci. Nutr.* 1997; 48:67-77).

Psyllium intake was reviewed for its effect on metabolic syndrome (Pal and Radavelli-Bagatini, *Obes Rev.* 2012; 13:1034-47). The authors concluded that the consumption of psyllium can provide benefits to many components of metabolic syndrome. Psyllium fiber appears to improve body weight in animals (Galisteo et al., *J. Nutr.* 2005; 135) but human studies remain controversial, with most showing no reduction in body weight or improvement in body composition following psyllium consumption (see, for example, Ziai et al., Rodriguez-Moran et al., Vuksan et al. and Tai et al., supra).

In terms of viscosity, PGX is a highly viscous soluble fiber that is three to five times more viscous than any known individual polysaccharide (Carabin et al., *Nutr. J.* 2009; 8:9). Psyllium has a similar physical appearance compared to PGX in its powder form but has a far lower viscosity than PGX.

Because PGX and psyllium are both viscous soluble fibers that absorb relatively large amounts of water and form gels that increase feelings of fullness (Vuksan et al., *Nutr. Metab. Cardiovasc. Dis.* 2009; 19:498-503), ingestion of PGX or psyllium can cause people to consume less food. The thickening of gut contents decreases intestinal passage rates, prolongs nutrient absorption and hence causes satiety (Dikeman et al., *J. Nutr.* 2006; 136:913-9). However, because PGX exhibits a much higher viscosity than psyllium, one skilled in the art would expect PGX to exhibit a higher viscosity compared to a composition comprising a mixture of PGX and psyllium. Further, given the increased effect of PGX on controlling or stabilizing postprandial glycemia/insulinemia as compared to the effect of psyllium, one skilled in the art would expect PGX to promote satiety, promote weight loss, or lower blood glucose levels much more effectively compared to a composition comprising psyllium alone or a composition comprising a mixture of PGX and psyllium.

In one aspect, the invention provides a dietary composition comprising (i) from about 40% to about 80% (w/w) of a fiber composition comprising glucomannan, xanthan gum, and alginate; and (ii) from about 10% to about 60% (w/w) psyllium. In one embodiment, the dietary composition comprises from about 50% to about 60% (w/w) of the fiber composition and from about 40% to about 50% (w/w) psyllium. As used herein, "glucomannan" refers to a water soluble fiber with β-(1,4)-linked-D-mannose and β-(1,4)-linked-D-glucose residues in approximately 3:1 ratio and various α-linked galactose end groups. It is most commonly isolated from konjac root (*Amorphophallus konjac*) but can also be isolated from other plant sources. "Xanthan gum" refers to a heteropolysaccharide containing glucose, mannose, potassium or sodium glucuronate, acetate and pyruvate. "Alginate" refers to a mixed polymer of mannuronic and guluronic acid. "Psyllium" is the common name for several members of the plant genus *Plantago*. Typically, psyllium is composed of a mixture of polysaccharides comprising hexoses, pentoses and uronic acids.

Referring to the fiber composition, the proportions of glucomannan, xanthan gum and alginate can be from about 50% to about 90% (w/w) glucomannan (such as from about 60% to about 80%, or from about 60% to about 90%, or from about 65% to about 75%, or from about 50% to about 80%, or from about 50% to about 70%, or about 70%), from about 10% to about 20% (w/w) xanthan gum (such as from about 11% to about 13%, or from about 13% to about 17%, or about 13%, or about 17%), and from about 10% to about 20% (w/w) alginate (such as from about 13% to about 17%, or about 13%, or about 17%). In some embodiments, the proportions of glucomannan, xanthan gum, and alginate in the fiber composition are about 70% (w/w) glucomannan, from about 13% to about 17% (w/w) xanthan gum, and from about 13% to about 17% (w/w) alginate.

The compositions of the invention comprise effective amounts of glucomannan, xanthan gum, alginate and psyllium. As used herein, an "effective amount" refers to an amount that produces the desired viscosity. Effective amounts of glucomannan, xanthan gum and alginate are proportionate amounts of each of these components that produce the desired viscosity when combined. Effective amounts of the fiber composition are amounts of the composition that produce the desired viscosity when ingested. The proportion of glucomannan, xanthan gum and alginate in the fiber composition is generally selected to produce a fiber composition that has an initial viscosity that is palatable, but that increases in viscosity substantially over a 15 to 60-minute time period and that maintains or increases in viscosity under gastric or intestinal conditions.

As used herein, the term "initial viscosity that is palatable" refers to a range of viscosity from about 1 centipoise (cps) to about 3,000 cps. Liquids with a viscosity of greater than about 3,000 cps are difficult to ingest and are therefore considered to be non-palatable. As used herein, "initial viscosity" refers to the viscosity of the dietary composition in a 100-fold (w/w) excess of water at a temperature between about 4° C. to about 25° C., for example, between about 16° C. and about 25° C., or equivalent conditions.

"Viscosity under gastric conditions" refers to the viscosity of the dietary composition in a 70-fold (w/w) excess of gastric fluid at a temperature between about 16° C. and about 25° C., or equivalent conditions. "Gastric fluid" refers to a solution having a pH of about 1.2 that is made by dissolving 2 g of NaCl and 3.2 g of pepsin in 7.0 mL of HCl and sufficient water to make 100 mL (see United States Pharmacopoeia). Gastric conditions can be simulated by adding 10 drops of phosphoric acid to 200 g of distilled water. "Viscosity under intestinal conditions" refers to the viscosity of the dietary composition in a 70-fold (w/w) excess of simulated intestinal fluid at a temperature between about 16° C. and about 25° C. or equivalent conditions.

"Simulated intestinal fluid" refers to a solution having a pH between about 7.5 and about 8.0 that is made as follows: 6.8 g of monobasic potassium phosphate is dissolved in 250 mL of water and mixed; 190 mL of 0.2 N NaOH and 400 mL of water are added. This is followed by adding 10 g of pancreatin, mixing, adjusting the solution with 0.2 N NaOH to a pH of 7.5±0.1 and diluting with water to 1000 mL (see United States Pharmacopoeia).

The dietary composition described herein generally has an initial viscosity in water of between about 1 cps and about 3,000 cps (such as from about 200 cps to about 1,000 cps or from about 400 cps to about 1,000 cps).

The fiber composition generally has an initial viscosity of between about 1 cps and about 3,000 cps (such as from about 200 cps to about 1,000 cps or from about 400 cps to about 1,000 cps). The fiber composition generally has a viscosity under gastric conditions of between about 600 cps and about 5000 cps (such as from about 1,000 cps to about 5,000 cps or from about 1,000 cps to about 3,000 cps) after about 30 minutes. The fiber composition generally has a viscosity under intestinal conditions of between about 1,500 cps and about 8,000 cps (such as from about 2,000 cps to about 6,000 cps or from about 2,500 cps to about 6,000 cps) after about 30 minutes. The fiber composition comprises effective amounts of glucomannan, xanthan gum, and alginate to produce an initial viscosity of from about 1 to about 3,000 cps and a least a three-fold increase in viscosity within 15 minutes after ingestion by a mammalian subject (e.g., under gastric conditions).

In some embodiments the composition is granulated. The dietary composition, the fiber composition, PGX and/or psyllium can be granulated separately or together. For example, the fiber composition can be granulated and then mixed or blended with psyllium. In another example, konjac, xanthan gum and sodium alginate can be granulated and then mixed or blended with psyllium. In another example, the fiber composition and psyllium can be granulated together. In yet another example, konjac, xanthan gum, sodium alginate and psyllium can be granulated together. As used herein, "granulation" refers to any process of size enlargement in which small particles are gathered together into larger, permanent aggregates. Granulation can be accomplished by agitation in mixing equipment, by compaction, extrusion, or globulation. The fiber composition can be granulated using various mesh sizes. The term "mesh" refers to the size of the particle as determined by its ability to pass through a screen having holes of defined dimensions. The mesh sizes used herein are Tyler equivalents, as set forth in Table 21-12 of the Chemical Engineers Handbook (5th ed., Perry & Chilton, eds.). The larger the granulation (i.e., the smaller the mesh size) of the fiber composition, the longer it takes for a desired viscosity to be attained. In some embodiments, the fiber composition is granulated using a combined mesh size by separating granulated materials by their particle size, then recombining the particle-size separated granules to give the desired viscosity profile. For example, a combined mesh size of 30 to 60 is obtained by combining granules of 30 mesh (about 600 microns), granules of about 40 mesh (about 400 microns) and granules of about 60 mesh (250 microns). For example, PGX 100 is a granulated fiber composition comprising glucomannan, xanthan gum and alginate, wherein the granules are not less than (NLT) 95% through #40 Mesh, measured using USP 786. PGX 300 is a granulated fiber composition comprising glucomannan, xanthan gum and alginate. PGX 300 is not more than (NMT) 3% on #20 Mesh; NLT 45% on #40 Mesh; NLT 35% on #60 Mesh; and NMT 4% through #60 mesh, measured using USP 786.

In some embodiments, the dietary composition includes at least one lipid or blend thereof, wherein the lipid or blend thereof comprises at least 20% (w/w) of the total fiber composition.

As used in accordance with this embodiment of the invention, a lipid is defined as a substance such as a fat, oil or wax that dissolves in alcohol but not in water. As used herein, the terms "fat" and "oil" are used interchangeably and comprise fatty acids.

In some embodiments, the lipid for use in the composition comprises a fat selected from the group consisting of a dairy fat (e.g., milk fat, butter fat), an animal fat (e.g., lard) or a vegetable fat (e.g., coconut oil, cocoa butter, or palm oil).

In some embodiments, the lipid for use in the composition comprises an edible oil or a mixture of oils. Such oils include vegetable oils (e.g., canola oil, soybean oil, palm kernel oil, olive oil, safflower oil, sunflower seed oil, flaxseed (linseed) oil, corn oil, cottonseed oil, peanut oil, walnut oil, almond oil, grape seed oil, evening primrose oil, coconut oil, borage oil and blackcurrant oil); marine oils (e.g., fish oils and fish liver oils), or a mixture thereof.

In some embodiments, the lipid for use in the composition comprises oils containing medium-chain triglycerides ("MCTs"), such as coconut oil, palm kernel oil and butter or medium-chain triglycerides in purified form. The addition of a lipid or blend thereof to the various embodiments described herein is effective to delay the viscous effects of the fiber compositions in water and is useful to prevent choking during oral administration in a subject while allowing for a high viscosity within a short time under gastric conditions (i.e., in vivo conditions, post consumption).

The compositions described herein can further comprise additional components. For example, the compositions can additionally comprise magnesium stearate, rice flour, xylitol, lecithin, medium chain triglycerides, colors, flavors, stevia and/or syloid silica. Exemplary compositions are described in EXAMPLES 1, 2 and 3.

The compositions described herein can further comprise an effective amount of a medication used for the treatment of diabetes, for example, metformin and/or sitagliptin. As used herein, "metformin" refers to metformin hydrochloride, (systematic (IUPAC) name N,N-dimethylimidodicarbonimidic diamide hydrochloride), which is an oral antihyperglycemic drug in the biguanide class used in the management of type II diabetes. Metformin hydrochloride USP, is a white crystalline compound with a molecular formula of $C_4H_{11}N_5$+HCl and a molecular weight of 165.63 and is freely soluble in water.

Metformin is sold under several trade names, including GLUCOPHAGE, RIOMET, FORTAMET, GLUMETZA, OBITMET, GLUFORMIN, DIANBEN, DIABEX and DIAFORMIN.

Metformin IR (immediate release) is available in available 500 mg, 850 mg and 1000 mg tablets. The maximum recommended daily dosage of metformin hydrochloride tablets is 2550 mg in adults and 2000 mg in pediatric patients (10-16 years old). Typically, adult dosing is 500 mg twice a day as a minimum up to a total of 2000 mg/day, given in divided doses. Dosing is determined on an individual basis, wherein fasting plasma glucose may be used to determine the therapeutic response to identify the minimum effective dose for the patient. Thereafter, glycosylated hemoglobin ($HbA_1c$) may be measured at intervals of approximately three months. The therapeutic goal is to decrease both fasting plasma glucose and glycosylated hemoglobin levels to normal or near normal by using the lowest effective dose, either when used as monotherapy or in combination with a fiber composition of the invention.

Metformin improves hyperglycemia by suppressing glucose production by the liver (Kirpichnikov, D., et al., *Ann Intern Med* 137(1):25-33 (2002)). In addition to suppressing hepatic glucose production, metformin increases insulin sensitivity, enhances peripheral glucose uptake, increases fatty acid oxidation and decreases absorption of glucose from the gastrointestinal tract (Collier, C., et al., *Am J Physiol Endorinol Metab* 291(1):E182-189 (2006)). Metformin is not metabolized and is cleared from the body by tubular secretion and excreted unchanged in the urine. The average half-life in plasma is 6.2 hours. See Bristol-Myers Squibb GLUCOPHAGE Label information, Aug. 27, 2008.

The usual synthesis of metformin involves the reaction of dimethylamine hydrochloride and 2-cyanoguanidine (dicyandiamide) with heating, as described in Werner, E., et al., *J Chem Soc Transactions* 121:1790-5 (1921); Shapiro, S., et al., *J Am Chem Soc* 81(9):2220-5 (1959), both of which are hereby incorporated herein by reference. As described in Patent FR 2322860 (1975) and Pharmaceutical Manufacturing Encyclopedia Vol. 3, Norwich, N.Y., p. 2208 (2007), both of which are hereby incorporated herein by reference, equimolar amounts of dimethylamine and 2-cyanoguanidine are dissolved in toluene with cooling to make a concentrated solution and an equimolar amount of hydrogen chloride is slowly added. The mixture begins to boil on its own and after cooling, metformin hydrochloride precipitates with a 96% yield.

As used herein, "sitagliptin" refers to sitagliptin and pharmaceutically acceptable salts thereof, e.g., sitagliptin phosphate. Sitagliptin (systematic IUPAC name (R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine) is an oral antihyperglycemic of the dipeptidyl peptidase-4 (DPP-4) inhibitor class, marketed under the trade name JANUVIA. This drug is used either alone or in combination with other oral antihyperglycemic agents such as metformin for the treatment of type II diabetes. There have been reports of pancreatitis (some fatal) in people treated with sitagliptin. See Olansky, L., et al., *J Diabetes Sci Technol* 4(1):228-9 (2010); Merck & Co. There have also been reports of worsening renal function after taking JANUVIA, including acute renal failure, sometimes requiring dialysis.

Sitagliptin was approved by the FDA in 2006 and is marketed in the U.S. as JANUVIA by Merck & Co. In 2007, the FDA approved an oral combination of sitagliptin and metformin marketed in the U.S. as JANUMET.

Sitagliptin works to competitively inhibit the enzyme dipeptidyl peptidase 4 (DPP-4), which breaks down the gluco-incretins GLP-1 (glucopgen-like peptide 1) and GIP (gastric inhibitory peptide), gastrointestinal hormones released in response to a meal (Herma, G., et al., *J Clin Pharmacol* 46(8):876-86 (2006)). By preventing GLP-1 and GIP inactivation, DPP-4 inhibitors increase the secretion of insulin, causing glucose uptake by cells, which decreases serum glucose levels and suppress the release of glucagon by the pancreas which drives blood glucose levels towards normal.

The recommended dosage of sitagliptin for an adult human subject is 100 mg once daily. Decreased dosages are recommended for patients with moderate to severe renal insufficiency.

JANUVIA tablets contain 25, 50 or 100 mg sitagliptin phosphate, which is described chemically as 7-[(3R)-3-amino-1-oxo-4-(2,4,5-trifluorophenyl)buty]-5,6,7,8-tetrahydro-3-(trifluoromethyl)-1,2,4-triazolo[4,3-a]pyrazine phosphate (1:1) monohydrate. The empirical formula is $C_{16}H_{15}F_6N_5O$—$H_3PO_4$—$H_2O$ and the molecular weight is 523.32. Sitagliptin phosphate monohydrate is a white crystalline non-hygroscopic powder. It is soluble in water. Synthesis of sitagliptin phosphate is described, e.g., in U.S. Pat. No. 6,699,871, incorporated herein by reference.

The dietary composition is prepared in a form suitable for oral use according to any method known in the art for the manufacture of oral compositions. In some embodiments, the dietary composition is contained in a soft gel capsule, compounded into a tablet, or formulated into a powder. For example, the composition can be prepared as tablets, troches, lozenges, aqueous or oily suspensions, dispersible/dispensable powders or granules (e.g., powders and granules that can be sprinkled on food), emulsions, hard or soft gel capsules, syrups, elixirs or enteral formulas, or controlled-release compositions. For oral consumption, the composition can be added to a food or a beverage. For example, a powdered form of the composition can be mixed with an ingestible liquid to form an aqueous beverage or mixed with cookie batter prior to baking. An exemplary formulation of the dietary composition is as hard gelatin capsules, each capsule comprising about 500 mg of the dietary composition.

In another aspect, the present invention provides a method for promoting satiety, promoting weight loss, lowering blood cholesterol levels or lowering blood glucose levels in a mammal, comprising administering to a mammal a dietary composition comprising (i) from about 40% to about 80% (w/w) of a fiber composition comprising glucomannan, xanthan gum, and alginate; and (ii) from about 10% to about 60% (w/w) psyllium, in an amount effective to promote satiety, promote weight loss, or lower blood glucose levels.

In one embodiment, the fiber composition comprises from about 50% to about 90% (w/w) glucomannan, from about 5% to about 20% (w/w) xanthan gum, and from about 5% to about 30% (w/w) alginate. In one embodiment, the fiber composition is granulated. In one embodiment, the fiber composition and psyllium are granulated. The fiber composition and psyllium can be granulated separately and then mixed or blended together or the fiber composition and psyllium can be granulated together.

In one embodiment, the fiber composition includes at least one lipid or blend thereof, wherein the lipid or blend thereof comprises at least 20% (w/w) of the total fiber composition. In one embodiment, the dietary composition is contained in a soft gel capsule, compounded into a tablet, or formulated into a powder.

The dietary composition described herein can be consumed before a meal, during a meal, or after a meal. The composition controls hunger and induces satiety by providing a high viscosity bolus in the stomach and gastrointestinal tract. For example, the composition maintains high viscosities under both the acidic conditions of the stomach and the alkaline conditions in the intestines. The composition further assists in the management of metabolic conditions by lowering blood glucose levels.

In another aspect, the present invention provides a food product for promoting satiety, promoting weight loss, lowering blood cholesterol levels and/or lowering blood glucose levels in a mammal comprising a dietary composition comprising (i) from about 40% to about 80% (w/w) of a fiber composition comprising glucomannan, xanthan gum, and alginate; and (ii) from about 10% to about 60% (w/w) psyllium. In one embodiment, the fiber composition comprises from about 50% to about 90% (w/w) glucomannan, from about 5% to about 20% (w/w) xanthan gum, and from about 5% to about 30% (w/w) alginate.

In one embodiment, the fiber composition is granulated. In one embodiment, the fiber composition and psyllium are granulated. The fiber composition and psyllium can be granulated separately and then mixed or blended together or the fiber composition and psyllium can be granulated together.

The food products described herein can be dietary supplements or meal replacements. In some embodiments, the food products are provided as, for example, shakes or smoothies. Typically, the food products of the invention comprise from about 2% to about 30% (such as from about 2% to about 20%, or from about 5% to about 15%, or from about 2% to about 10%) of a fiber composition comprising glucomannan, xanthan gum, and alginate, or from about 2% to about 30% (such as from about 2% to about 20%, or from about 5% to about 15%, or from about 2% to about 10%) of the dietary composition comprising the fiber composition and psyllium. Typically, the food products comprise between about 2 grams and about 20 grams of the fiber composition or the dietary composition comprising the fiber composition and psyllium per serving (such as between about 3 to 8 grams or between about 3 and about 6 grams per serving). In some embodiments, the food products of the invention comprise about 9% (w/w) of the fiber composition or about 9% (w/w) of dietary composition comprising the fiber composition and psyllium.

The food products of the invention can further contain additional components such as proteins or amino acids, carbohydrates, lipids, vitamins, minerals and cofactors, natural or artificial flavors, coloring agents or other coloring additives and preservatives. The term "vitamins" includes, but is not limited to, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term "vitamins" are cofactors and coenzymes such as coenzymes include thiamine pyrophosphates (TPP), flavin mononucleotide (FMM), flavin adenine dinucleotide (FAD), nicotinamide adenine dinucleotide (NAD), nicotinamide adenine dinucleotide phosphate (NADP), Coenzyme A (CoA), pyridoxal phosphate, biocytin, tetrahydrofolic acid, coenzyme B12, lipoyllysine, 11-cis retinal and 1,25-dihydroxycholecalciferol. The term "vitamins" also includes choline, carnitine and alpha, beta and gamma carotenes. The term "minerals" refers to inorganic substances, metals, and the like, required in the human diet, including, but not limited to, calcium, iron, zinc, selenium, copper, iodine, magnesium, phosphorus, chromium, manganese, potassium, and the like, and mixtures thereof. The mineral can be in the form of a salt, an oxide, or a chelated salt.

Coloring agents can include, but are not limited to, titanium dioxide and dyes suitable for food such as those known as FD&C dyes and natural coloring agents such as grape skin extract, beet red powder, beta carotene, annatto, carmine, turmeric, chlorophyll and paprika. The amount of coloring used can range from about 0.0% to about 3.5% dry weight of the total composition, depending on the saturation of the color.

Flavors incorporated in the composition can be selected from, for example, synthetic flavor oils and flavoring aromatics and/or natural oils, extracts from plants, leaves, flowers and fruits, and combinations thereof. These can include, but are not limited to, cinnamon oil, oil of wintergreen, peppermint oils, clove oil, bay oil, anise oil, eucalyptus, thyme oil, cedar leaf oil, oil of nutmeg, oil of sage, oils of citrus fruits (including, but not limited to, lemon and orange) oil of bitter almonds and cassia oil. Suitable flavors include, but are not limited to, vanilla, chocolate, mocha, coffee, ice cream, citrus (including lemon, orange, grape, lime and grapefruit), apple, pear, peach, mango, strawberry, raspberry, cherry, plum, pineapple and apricot. The amount of flavoring can depend on a number of factors, including the organoleptic effect desired. Flavors can be present in an amount ranging from about 0% to about 10.0% dry weight based upon the dry weight of the composition.

Some embodiments of the invention provide food products containing less than 28 grams of whey protein or less than 8.9 grams of fructose. Some embodiments of the invention provide food products containing more than 0.9 grams of a medium chain triglyceride.

In one embodiment, the food product is a dietary supplement or a meal replacement product. In one embodiment, the food product is compounded to provide a daily dose of from about 5 grams to about 25 grams of the dietary composition, or from about 5 grams to about 25 grams of the dietary composition. The dietary composition can be combined with any type of food product, including solid, liquid, or semi-solid food products. Exemplary solid food products include, but are not limited to grains (e.g., rice, cereal (hot or cold)), granola, oatmeal, baked goods (bread, cookies, muffins, cakes and others), pasta (including noodles made with rice or other grains), meat (e.g., poultry, beef, pork, lamb and fish), dairy products (e.g., milk, yogurt, cheese, ice cream and butter) and non-dairy products (e.g., almond milk, cashew milk, pumpkin seed milk, flax milk, hazelnut milk, hemp milk, coconut milk, soy milk, oat milk, quinoa milk, rice milk and margarine). Exemplary liquid or semi-liquid food products include, but are not limited to, meal replacement drinks, fruit juices, soups (including dry soup mixes), dietary supplements and smoothies.

The fiber composition can be added to the food product prior to consumption using any suitable method. For example, the fiber composition can be baked into the food product, can be mixed with the food product, or sprinkled onto the food product.

The following examples merely illustrate the best mode now contemplated for practicing this invention but should not be construed to limit the invention.

Example 1

This example describes the viscosity profile of exemplary compositions comprising PGX, psyllium and a mixture of PGX and psyllium in water. The following samples were prepared.
Sample 1: 3 g psyllium and 2.5 g PGX (Lot No. 903023; Inovobiologic Inc., Calgary, Alberta, Canada)
Sample 2: 3 g psyllium
Sample 3: 2.5 g PGX (Lot No. 903023)
Sample 4: 3 g psyllium
Sample 5: 3 g psyllium and 2.5 g PGX (Lot No. 903023)

Each sample was mixed in 350 g deionized (DI) water and blended using a no. 3 spindle for 30 seconds at 4,000 RPM, followed by 30 seconds at 8,000 RPM. The samples were placed in a 25° C. water bath and viscosity readings were taken at the following time intervals: 5, 10, 15, 20, 30, 60, 90, 120, 150, 180, 210 and 240 minutes. The viscosity data for each of samples 1-5 are shown in TABLE 1. The pH for each sample 1-5 was 6.3, 6.21, 6.85, 5.8 and 6.48, respectively.

TABLE 1. Referring to FIG. 1, Samples 2 and 4 exhibited a viscosity of 0 cps from time=0 until time=240 minutes. Sample 3, composed of PGX alone, reached a maximum viscosity of about 78,000 cps at time=240 minutes. Samples 1 reached a maximum viscosity of about 97,000 cps at time=180 minutes. Sample 5 reached a maximum viscosity of about 21,300 cps at time=150 minutes. The results demonstrate that the compositions comprising PGX alone or a combination of PGX and psyllium exhibit a higher viscosity in water as compared to compositions comprising psyllium alone.

Example 2

This example describes the viscosity profile of representative compositions comprising non-granulated PGX or a mixture of non-granulated PGX and psyllium in water.

Experiment 1

A sample containing 57 g SLIMSTYLES base mix with no PGX (Lot No. 22117160517; Inovobiologic Inc.), 4 g PGX 100 (Lot No. 733333; Inovobiologic Inc.) and 3.4 g psyllium was mixed with 350 g DI water and blended using a no. 3 spindle for 30 seconds at 4,000 RPM, followed by 30 seconds at 8,000 RPM. The sample was placed in a 25° C. water bath and viscosity readings were taken at time=5, 10, 15, 20, 30, 60, 90, 120, 150, 180, 210 and 240 minutes. The pH of the sample was 6.5 after 240 minutes. The viscosity data in cps and pH are shown in TABLE 2.

TABLE 2

| Time | Spindle | RPM | Viscosity |
| --- | --- | --- | --- |
| 5 | 3 | 20 | 2,680 |
| 10 | 3 | 1 | 14,610 |
| 15 | 3 | 1 | 18,330 |
| 20 | 3 | 1 | 23,970 |
| 30 | 3 | 1 | 30,520 |
| 60 | 3 | 1 | 45,490 |
| 90 | 3 | 1 | 64,140 |
| 120 | 3 | 1 | 76,210 |
| 150 | 3 | 1 | 80,250 |
| 180 | 3 | 1 | 80,990 |
| 210 | 3 | 1 | 78,660 |
| 240 | 3 | 1 | 76,770 |

TABLE 1

| Time (minutes) | Sample 1 | | Sample 2 | | Sample 3 | | Sample 4 | | Sample 5 | |
| --- | --- | --- | --- | --- | --- | --- | --- | --- | --- | --- |
| | RPM | Viscosity | RPM | Viscosity | RPM | Viscosity | RPM | Viscosity | RPM | Viscosity |
| 5 | 20 | 1,100 | 100 | 40 | 100 | 110 | 100 | 20 | 20 | 760 |
| 10 | 20 | 1,920 | 100 | 70 | 20 | 540 | 100 | 30 | 20 | 1,420 |
| 15 | 20 | 2,980 | 100 | 70 | 20 | 790 | 100 | 30 | 10 | 2,260 |
| 20 | 1 | 17,210 | 100 | 80 | 2.5 | 3210 | 100 | 30 | 2.5 | 6,080 |
| 30 | 1 | 26,690 | 100 | 60 | 1 | 11,870 | 100 | 30 | 1 | 10,700 |
| 60 | 1 | 48,120 | 100 | 50 | 1 | 29,410 | 100 | 30 | 1 | 15,330 |
| 90 | 1 | 69,080 | 100 | 50 | 1 | 49,140 | 100 | 30 | 1 | 19,590 |
| 120 | 1 | 84,600 | 100 | 50 | 1 | 62,720 | 100 | 30 | 1 | 21,100 |
| 150 | 1 | 86,720 | 100 | 50 | 1 | 70,650 | 100 | 30 | 1 | 21,330 |
| 180 | 1 | 96,670 | 100 | 50 | 1 | 74,040 | 100 | 30 | 1 | 19,940 |
| 210 | 1 | 84,500 | 100 | 50 | 1 | 75,790 | 100 | 30 | 1 | 18,580 |
| 240 | 1 | 76,320 | 100 | 50 | 1 | 77,840 | 100 | 30 | 1 | 17,820 |

Figure 2:
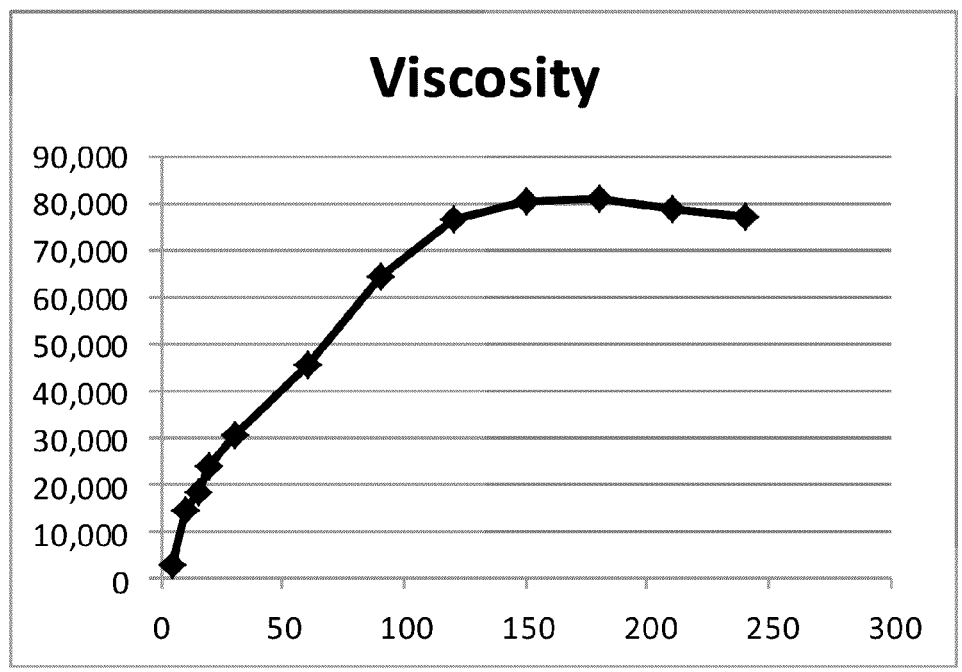
FIG. 2 graphically illustrates the viscosity profile of an exemplary composition comprising 4 g PGX and 3.4 g psyllium.

FIG. 1 graphically illustrates the viscosity profiles of representative compositions comprising PGX 100, psyllium and a combination of PGX 100 and psyllium shown in FIG. 2 graphically illustrates the viscosity profile of the exemplary composition comprising 4 g PGX 100 and 3.4 g psyllium shown in TABLE 2. Referring to FIG. 2, the sample reaches a maximum viscosity of about 81,000 cps at time=180 minutes.

Experiment 2

A sample containing 57 g SLIMSTYLES base mix with no PGX (Lot No. 22117160517), 4 g PGX 100 (Lot No. 733333) and 2.72 g psyllium was mixed with 350 g DI water and blended using a no. 3 spindle for 30 seconds at 4,000 RPM, followed by 30 seconds at 8,000 RPM. The sample was placed in a 25° C. water bath and viscosity readings were taken at time=5, 10, 15, 20, 30, 60, 90, 120, 150, 180, 210 and 240 minutes. The pH of the sample was 6.5 after 240 minutes. The viscosity data are shown in TABLE 3.

TABLE 3

| Time | Spindle | RPM | Viscosity |
|---|---|---|---|
| 5 | 3 | 50 | 890 |
| 10 | 3 | 10 | 2,630 |
| 15 | 3 | 5 | 6,860 |
| 20 | 3 | 1 | 16,810 |
| 30 | 3 | 1 | 20,750 |
| 60 | 3 | 1 | 34,790 |
| 90 | 3 | 1 | 46,390 |
| 120 | 3 | 1 | 63,210 |
| 150 | 3 | 1 | 66,810 |
| 180 | 3 | 1 | 69,420 |
| 210 | 3 | 1 | 70,600 |
| 240 | 3 | 1 | 68,460 |

Figure 3:
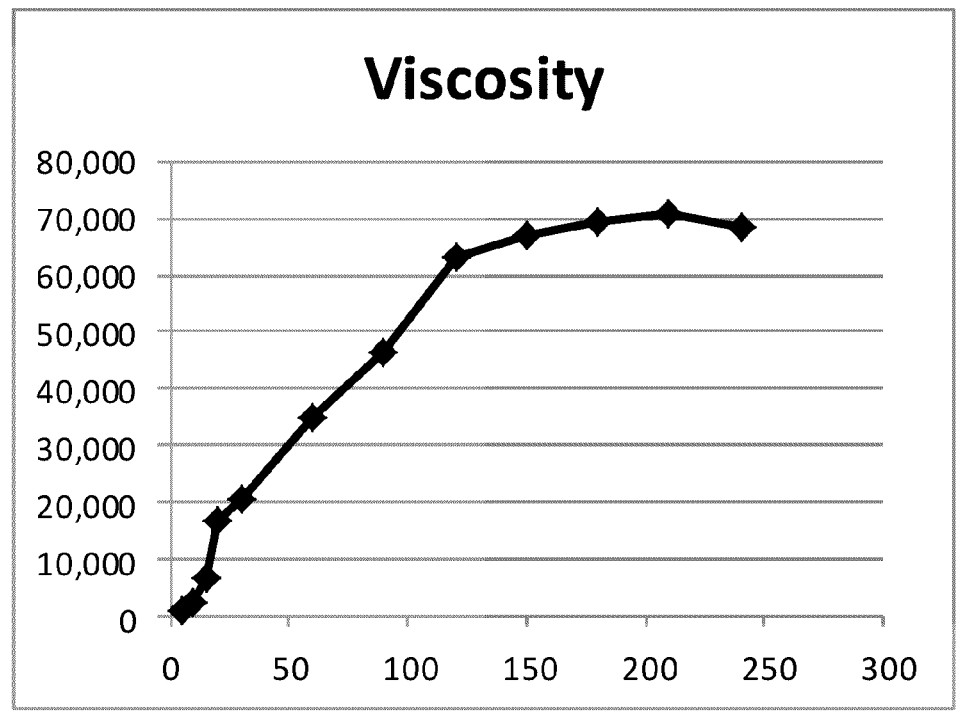
FIG. 3 graphically illustrates the viscosity profile of an exemplary composition comprising 4 g PGX and 2.72 g psyllium.

FIG. 3 graphically illustrates the viscosity profile of the exemplary composition comprising 4 g PGX 100 and 2.72 g psyllium shown in TABLE 3. Referring to FIG. 3, the sample reaches a maximum viscosity of about 71,000 cps at time=210 minutes.

Experiment 3

A sample containing 57 g SLIMSTYLES base mix and 4 g PGX (French Vanilla flavour; Lot No. 748548) was mixed with 350 g DI water and blended using a no. 3 spindle for 30 seconds at 4,000 RPM, followed by 30 seconds at 8,000 RPM. The sample was placed in a 25° C. water bath and viscosity readings were taken at time=5, 10, 15, 20, 30, 60, 90, 120, 150, 180, 210 and 240 minutes. The pH of the sample was 6.7 after 240 minutes. The viscosity data are shown in TABLE 4.

TABLE 4

| Time | Spindle | RPM | Viscosity |
|---|---|---|---|
| 5 | 3 | 100 | 350 |
| 10 | 3 | 100 | 680 |
| 15 | 3 | 20 | 1,750 |
| 20 | 3 | 10 | 3,390 |
| 30 | 3 | 10 | 4,370 |
| 60 | 3 | 1 | 22,370 |
| 90 | 3 | 1 | 27,150 |
| 120 | 3 | 1 | 31,080 |
| 150 | 3 | 1 | 34,960 |
| 180 | 3 | 1 | 39,560 |
| 210 | 3 | 1 | 41,250 |
| 240 | 3 | 1 | 44,330 |

Figure 4:
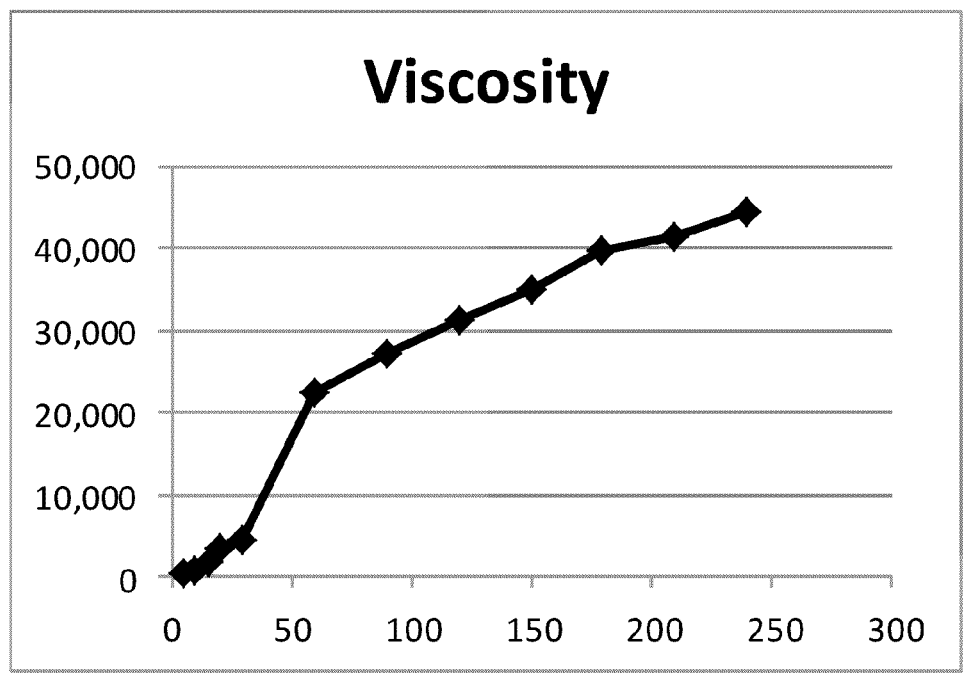
FIG. 4 graphically illustrates the viscosity profile of an exemplary composition comprising 5 g PGX.

FIG. 4 graphically illustrates the viscosity profile of the exemplary composition comprising 5 g PGX shown in TABLE 4. Referring to FIG. 4, the sample reaches a maximum viscosity of about 44,000 cps at time=240 minutes.

Experiment 4

A sample containing 57 g SLIMSTYLES base mix with no PGX (Lot No. 22117160517), 3 g PGX 100 (Lot No. 733333) and 3.4 g psyllium was mixed with 350 g DI water and blended using a no. 3 spindle for 30 seconds at 4,000 RPM, followed by 30 seconds at 8,000 RPM. The sample was placed in a 25° C. water bath and viscosity readings were taken at time=5, 10, 15, 20, 30, 60, 90, 120, 150, 180, 210 and 240 minutes. The pH of the sample was 6.5 after 240 minutes. The viscosity data are shown in TABLE 5.

TABLE 5

| Time | Spindle | RPM | Viscosity |
|---|---|---|---|
| 5 | 3 | 100 | 420 |
| 10 | 3 | 50 | 1,030 |
| 15 | 3 | 20 | 2,130 |
| 20 | 3 | 20 | 2,270 |
| 30 | 3 | 20 | 3,040 |
| 60 | 3 | 1 | 15,100 |
| 90 | 3 | 1 | 18,650 |
| 120 | 3 | 1 | 20,890 |
| 150 | 3 | 1 | 22,570 |
| 180 | 3 | 1 | 21,240 |
| 210 | 3 | 1 | 20,260 |
| 240 | 3 | 1 | 19,040 |

Figure 5:
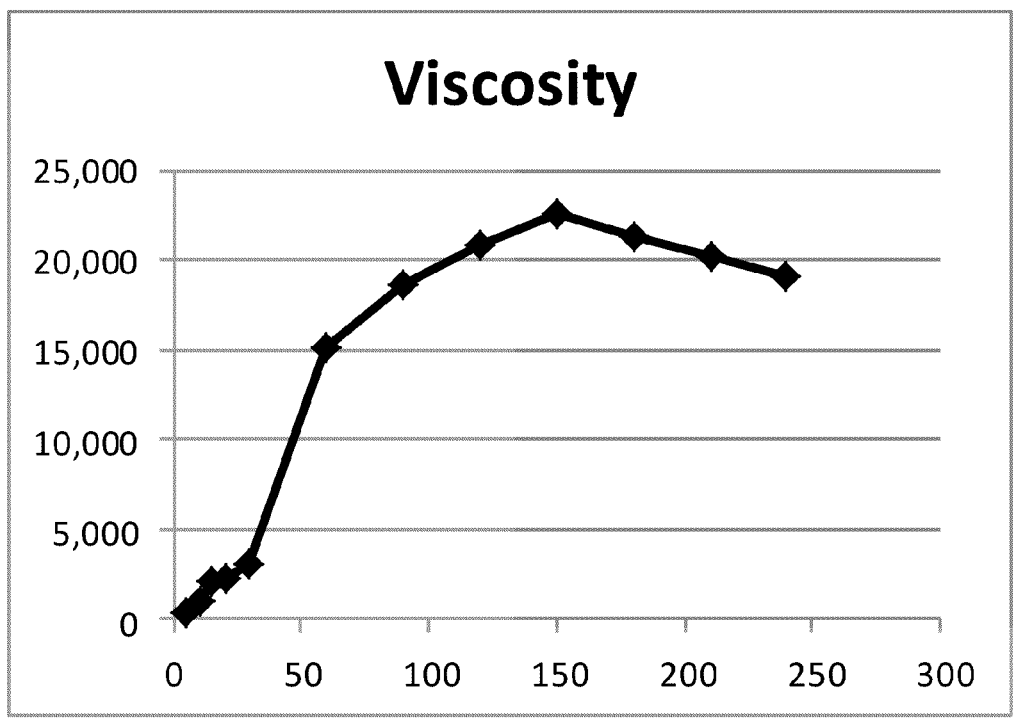
FIG. 5 graphically illustrates the viscosity profile of an exemplary composition comprising 3 g PGX and 3.4 g psyllium.

FIG. 5 graphically illustrates the viscosity profile of the exemplary composition comprising 3 g PGX 100 and 3.4 g psyllium shown in TABLE 5. Referring to FIG. 5, the sample reaches a maximum viscosity of about 23,000 cps at time=150 minutes.

Experiment 5

A sample containing 57 g SLIMSTYLES base mix with no PGX (Lot No. 22117160517), 3.5 g PGX 100 (Lot No. 733333) and 3.4 g psyllium was mixed with 350 g DI water and blended using a no. 3 spindle for 30 seconds at 4,000 RPM, followed by 30 seconds at 8,000 RPM. The sample was placed in a 25° C. water bath and viscosity readings were taken at time=5, 10, 15, 20, 30, 60, 90, 120, 150, 180, 210 and 240 minutes. The pH of the sample was 6.5 after 240 minutes. The viscosity data are shown in TABLE 6.

TABLE 6

| Time | Spindle | RPM | Viscosity |
|---|---|---|---|
| 5 | 3 | 100 | 530 |
| 10 | 3 | 20 | 2,100 |
| 15 | 3 | 20 | 2,670 |
| 20 | 3 | 10 | 4,360 |
| 30 | 3 | 5 | 7,780 |
| 60 | 3 | 1 | 23,970 |
| 90 | 3 | 1 | 33,570 |
| 120 | 3 | 1 | 38,460 |
| 150 | 3 | 1 | 41,390 |
| 180 | 3 | 1 | 42,240 |
| 210 | 3 | 1 | 40,780 |
| 240 | 3 | 1 | 40,230 |

Figure 6:
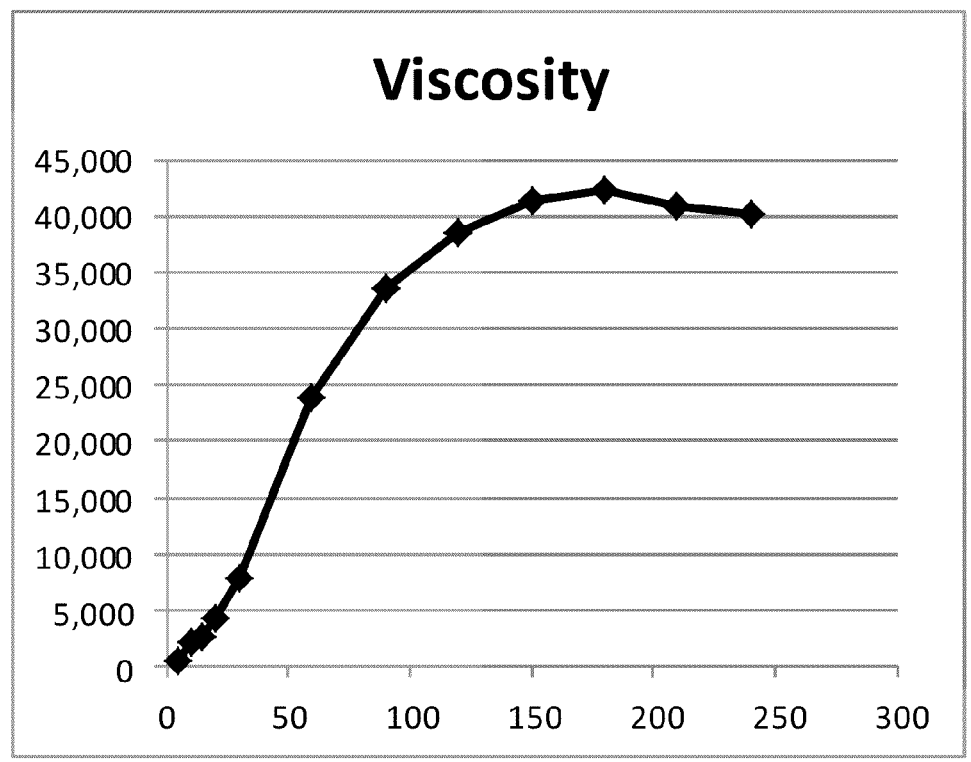
FIG. 6 graphically illustrates the viscosity profile of an exemplary composition comprising 3.5 g PGX and 3.4 g psyllium.

FIG. 6 graphically illustrates the viscosity profile of the exemplary composition comprising 3.5 g PGX 100 and 3.4 g psyllium shown in TABLE 6. Referring to FIG. 6, the sample reaches a maximum viscosity of about 42,000 cps at time=180 minutes.

Experiment 6

A sample containing 57 g SLIMSTYLES base mix with no PGX (Lot No. 22117160517), 3.5 g PGX 100 (Lot No.

733333) and 2.72 g psyllium was mixed with 350 g DI water and blended using a no. 3 spindle for 30 seconds at 4,000 RPM, followed by 30 seconds at 8,000 RPM. The sample was placed in a 25° C. water bath and viscosity readings were taken at time=5, 10, 15, 20, 30, 60, 90, 120, 150, 180, 210 and 240 minutes. The pH of the sample was 6.5 after 240 minutes. The viscosity data are shown in TABLE 7.

TABLE 7

| Time | Spindle | RPM | Viscosity |
|------|---------|-----|-----------|
| 5 | 3 | 100 | 420 |
| 10 | 3 | 50 | 1,020 |
| 15 | 3 | 20 | 2,260 |
| 20 | 3 | 20 | 2,720 |
| 30 | 3 | 5 | 6,920 |
| 60 | 3 | 1 | 21,680 |
| 90 | 3 | 1 | 31,810 |
| 120 | 3 | 1 | 36,180 |
| 150 | 3 | 1 | 37,970 |
| 180 | 3 | 1 | 39,740 |
| 210 | 3 | 1 | 38,340 |
| 240 | 3 | 1 | 39,040 |

Figure 7:
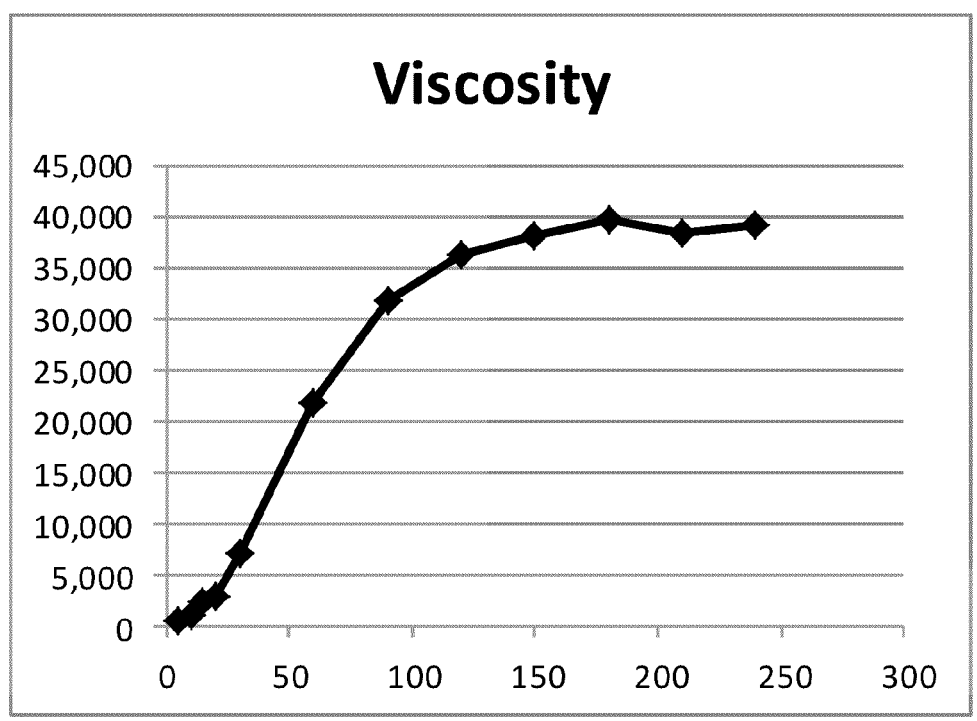
FIG. 7 graphically illustrates the viscosity profile of an exemplary composition comprising 3.5 g PGX and 2.72 g psyllium.

FIG. 7 graphically illustrates the viscosity profile of the exemplary composition comprising 3.5 g PGX 100 and 2.72 g psyllium shown in TABLE 7. Referring to FIG. 7, the sample reaches a maximum viscosity of about 40,000 cps at time=180 minutes.

Experiment 7

A sample containing 57 g SLIMSTYLES base mix with no PGX (Lot No. 22117160517), 3.75 g PGX 100 (Lot No. 733333) and 3.4 g psyllium was mixed with 350 g DI water and blended using a no. 3 spindle for 30 seconds at 4,000 RPM, followed by 30 seconds at 8,000 RPM. The sample was placed in a 25° C. water bath and viscosity readings were taken at time=5, 10, 15, 20, 30, 60, 90, 120, 150, 180, 210 and 240 minutes. The pH of the sample was 6.5 after 240 minutes. The viscosity data are shown in TABLE 8.

TABLE 8

| Time | Spindle | RPM | Viscosity |
|------|---------|-----|-----------|
| 5 | 3 | 50 | 1,220 |
| 10 | 3 | 1 | 11,720 |
| 15 | 3 | 1 | 15,250 |
| 20 | 3 | 1 | 17,610 |
| 30 | 3 | 1 | 22,540 |
| 60 | 3 | 1 | 41,410 |
| 90 | 3 | 1 | 54,380 |
| 120 | 3 | 1 | 59,910 |
| 150 | 3 | 1 | 61,750 |
| 180 | 3 | 1 | 65,360 |
| 210 | 3 | 1 | 61,730 |
| 240 | 3 | 1 | 56,320 |

As shown above, the sample reaches a maximum viscosity of about 65,000 cps at time=180 minutes.

Experiment 8

A sample containing 57 g SLIMSTYLES base mix with no PGX (Lot No. 22117160517), 3.75 g PGX 100 (Lot No. 733333) and 2.72 g psyllium was mixed with 350 g DI water and blended using a no. 3 spindle for 30 seconds at 4,000 RPM, followed by 30 seconds at 8,000 RPM. The sample was placed in a 25° C. water bath and viscosity readings were taken at time=5, 10, 15, 20, 30, 60, 90, 120, 150, 180, 210 and 240 minutes. The pH of the sample was 6.5 after 240 minutes. The viscosity data are shown in TABLE 9.

TABLE 9

| Time | Spindle | RPM | Viscosity |
|------|---------|-----|-----------|
| 5 | 3 | 100 | 500 |
| 10 | 3 | 10 | 2,710 |
| 15 | 3 | 5 | 4,960 |
| 20 | 3 | 1 | 10,460 |
| 30 | 3 | 1 | 14,440 |
| 60 | 3 | 1 | 28,010 |
| 90 | 3 | 1 | 39,090 |
| 120 | 3 | 1 | 47,900 |
| 150 | 3 | 1 | 51,220 |
| 180 | 3 | 1 | 52,150 |
| 210 | 3 | 1 | 50,500 |
| 240 | 3 | 1 | 48,990 |

As shown above, the sample reaches a maximum viscosity of about 52,000 cps at time=180 minutes.

Figure 8:
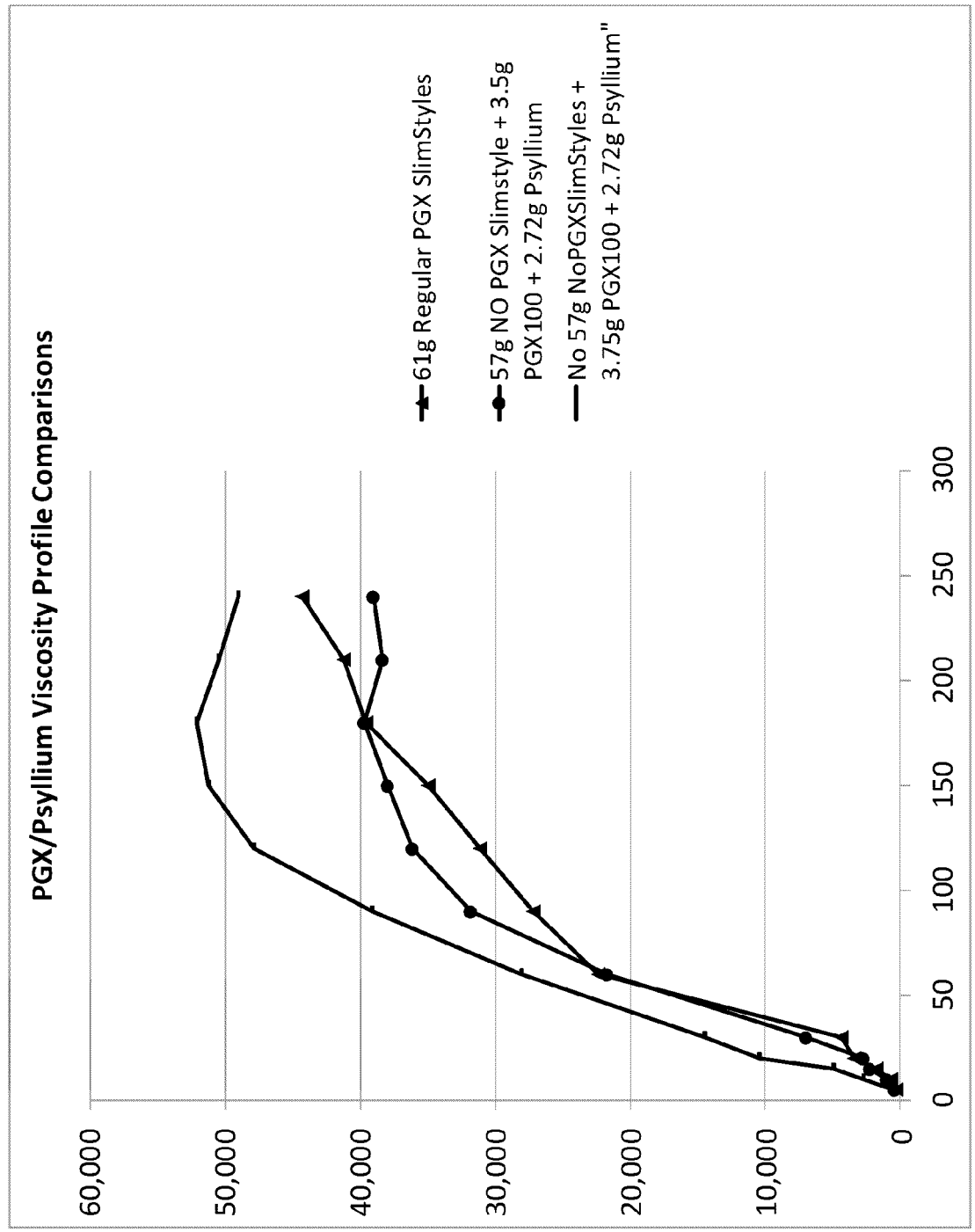
FIG. 8 graphically illustrates the viscosity profiles of exemplary compositions comprising PGX or a combination of PGX and psyllium.

FIG. 8 is a graphical representation of the viscosity data obtained from the sample compositions described in Experiments 3, 6 and 8, above. The composition described in Experiment 3 contains 57 g SLIMSTYLES base mix and 5 g PGX. The composition described in Experiment 6 contains 57 g SLIMSTYLES base mix with no PGX, 3.5 g PGX 100 and 2.72 g psyllium. The composition described in Experiment 8 contains 57 g SLIMSTYLES with no PGX, 3.75 g PGX 100 and 2.72 g psyllium. Referring to FIG. 8, all three sample compositions demonstrate a rapid increase in viscosity and reach a maximum viscosity at around 180 minutes, with the composition described in Example 2, Experiment 8 (57 g SLIMSTYLES with no PGX, 3.75 g PGX 100 and 2.72 g psyllium) reaching the highest viscosity of the three compositions.

The results are surprising because one skilled in the art would expect that a composition comprising PGX alone would exhibit a higher viscosity than a composition comprising PGX and psyllium. Instead, the inventors unexpectedly discovered that the compositions comprising PGX and psyllium exhibit a higher viscosity than the composition comprising PGX alone. The results suggest that PGX and psyllium have a complimentary, possibly synergistic effect to produce a higher viscosity than PGX alone.

Example 3

This example describes the viscosity profile of representative compositions comprising granulated or non-granulated PGX and psyllium in water.

Experiment 1

The following samples were prepared.
Sample 1: 62 g regular SLIMSTYLES (57 g SLIMSTYLES base mix and 5 g PGX) (Lot No. 748283; Inovobiologic Inc.)
Sample 2: Non-granulated
    2.83 g psyllium
    2.17 g non-granulated PGX 300 (Lot No. 19447151124; Inovobiologic Inc.)
    57 g SLIMSTYLES base mix with no PGX (Lot No. 20556160203)
Sample 3: Granulated
    2.83 g psyllium
    2.17 g granulated PGX 300 (Lot No. 19447151124)

57 g SLIMSTYLES base mix with no PGX (Lot No. 20556160203)

Sample 4: 57 g SLIMSTYLES base mix with no PGX (Lot No. 20556160203)

Each sample was mixed in 350 g deionized (DI) water and blended using a no. 3 spindle for 30 seconds at 4,000 RPM, followed by 30 seconds at 8,000 RPM. The samples were placed in a 25° C. water bath and viscosity readings were taken at the following time intervals: 5, 10, 15, 20, 30, 60, 90, 120, 150, 180, 210 and 240 minutes.

Figure 9:
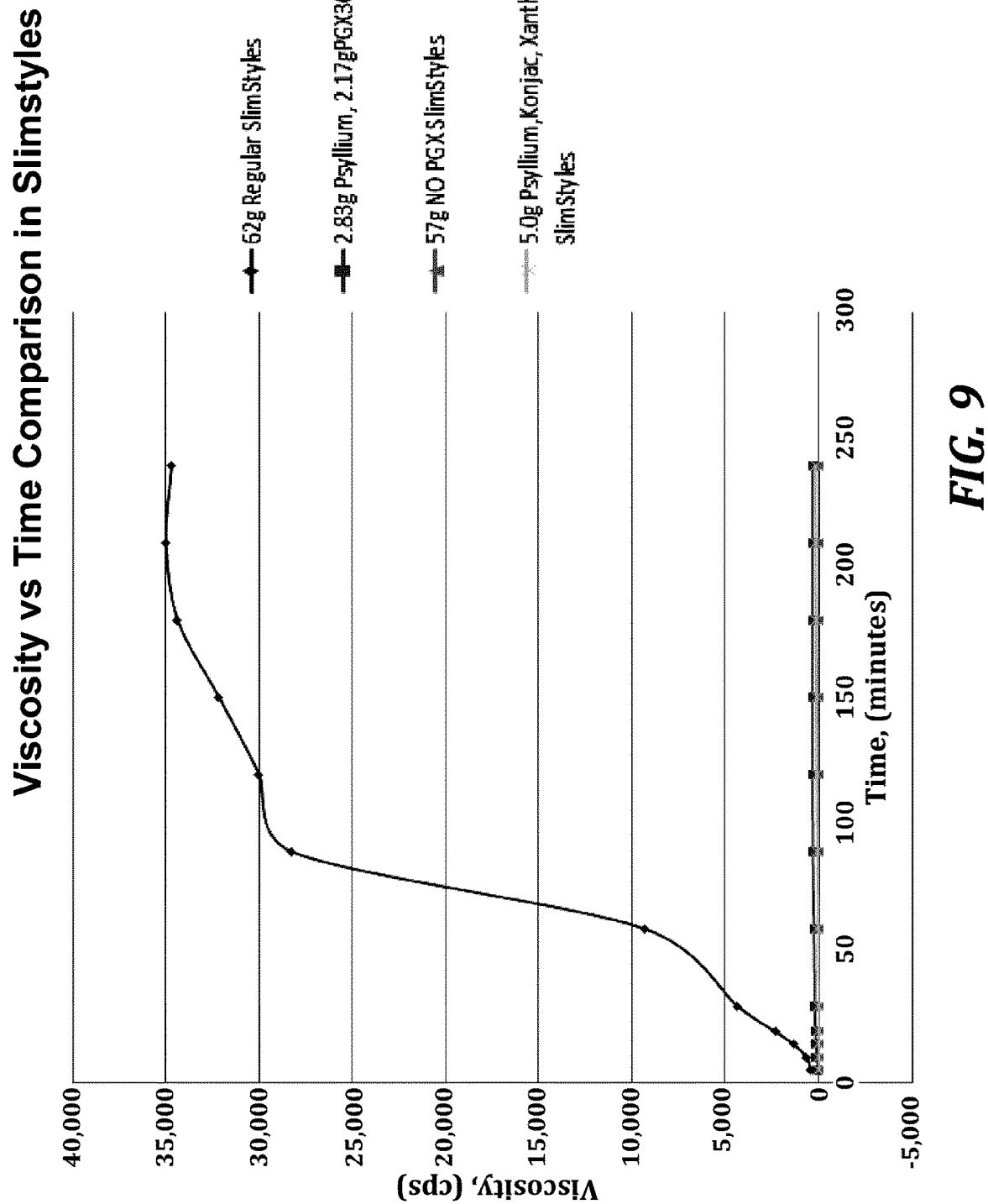
FIG. 9 graphically illustrates the viscosity profiles of representative compositions comprising PGX and combinations of PGX and psyllium.

FIG. 9 graphically illustrates the viscosity profiles of the compositions in Samples 1-4 above. Referring to FIG. 9, Sample 1 comprising regular SLIMSTYLES exhibited a higher viscosity than Sample 4 comprising SLIMSTYLES base mix with no PGX.

Experiment 2

The following samples were prepared.
Sample 1: Granulated
  57 g SLIMSTYLES base mix with no PGX (Lot No. 20556160203)
  5 g granulated PGX 300 (Lot. No. 19447151124)
  3.4 g psyllium
Sample 2: Non-granulated
  57 g SLIMSTYLES base mix with no PGX (Lot 20556160203)
  5 g non-granulated PGX 100 (Lot No. 733333)
Sample 3: Non-granulated
  57 g SLIMSTYLES base mix with no PGX (Lot 20556160203)
  5 g non-granulated PGX 300 (Lot No. 19447151124)
Sample 4: 62 g regular SLIMSTYLES (57 g SLIMSTYLES base mix and 5 g PGX)
Sample 5: Granulated
  57 g SLIMSTYLES base mix with no PGX (Lot No. 20556160203)
  2.17 g granulated PGX 300 (Lot. No. 19447151124)
  2.83 g psyllium
Sample 6: Granulated
  57 g SLIMSTYLES base mix with no PGX (Lot No. 20556160203)
  2.17 g granulated PGX 100 (Lot. No. 733333)
  2.83 g psyllium Each sample was mixed in 350 g deionized (DI) water and blended using a no. 3 spindle for 30 seconds at 4,000 RPM, followed by 30 seconds at 8,000 RPM. The samples were placed in a 25° C. water bath and viscosity readings were taken at the following time intervals: 5, 10, 15, 20, 30, 60, 90, 120, 150, 180, 210 and 240 minutes.

Figure 10:
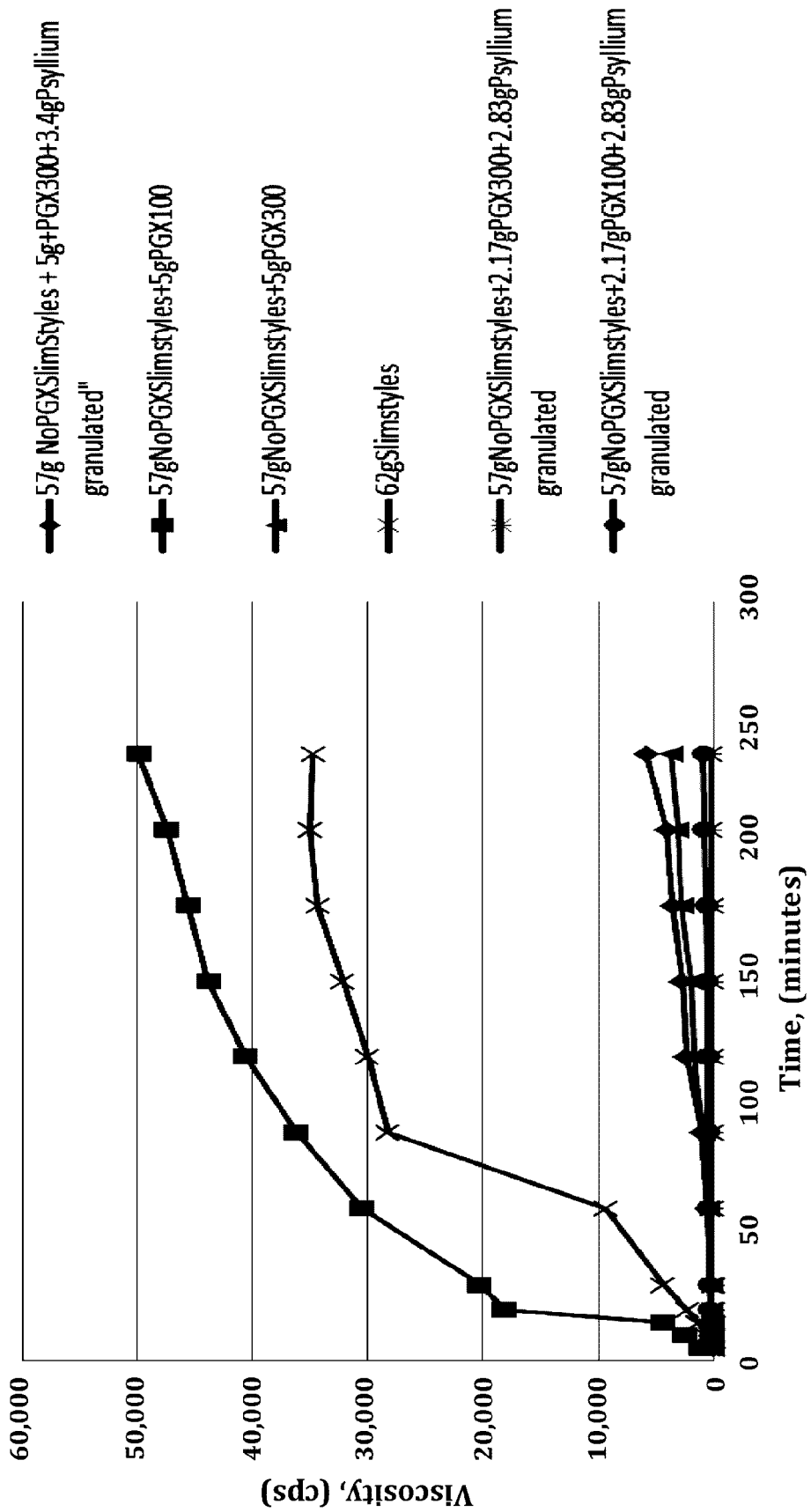
FIG. 10 graphically illustrates the viscosity profiles of representative compositions comprising PGX and combinations of PGX and psyllium, both granulated and non-granulated.

FIG. 10 graphically illustrates the viscosity profiles of the compositions in Samples 1-6 above. Referring to FIG. 10, Sample 2 comprising SLIMSTYLES and non-granulated PGX 100 developed the highest viscosity over time compared to the other samples. Sample 4 comprising regular SLIMSTYLES developed the second highest viscosity. As further shown in FIG. 10, SLIMSTYLES with PGX 100 has a higher viscosity profile than SLIMSTYLES with PGX 300. Comparing Samples 1 and 3, psyllium increases the viscosity profile of the SLIMSTYLES and PGX 300 composition. Reducing PGX greatly reduces the viscosity profile, indicating that PGX is a stronger thickening agent than psyllium.

Experiment 3

The following samples were prepared.
Sample 1: Non-granulated
  57 g SLIMSTYLES base mix with no PGX (Lot No. 20556160203)
  3.4 g psyllium
Sample 2: Granulated
  57 g SLIMSTYLES base mix with no PGX (Lot 20556160203)
  5 g granulated PGX 100 (Lot No. 733333)
  3.4 g psyllium
Sample 3: 62 g regular SLIMSTYLES (57 g SLIMSTYLES base mix and 5 g PGX; Lot No. 748283)

Each sample was mixed in 350 g deionized (DI) water and blended using a no. 3 spindle for 30 seconds at 4,000 RPM, followed by 30 seconds at 8,000 RPM. The samples were placed in a 25° C. water bath and viscosity readings were taken at the following time intervals: 5, 10, 15, 20, 30, 60, 90, 120, 150, 180, 210 and 240 minutes.

Figure 11:
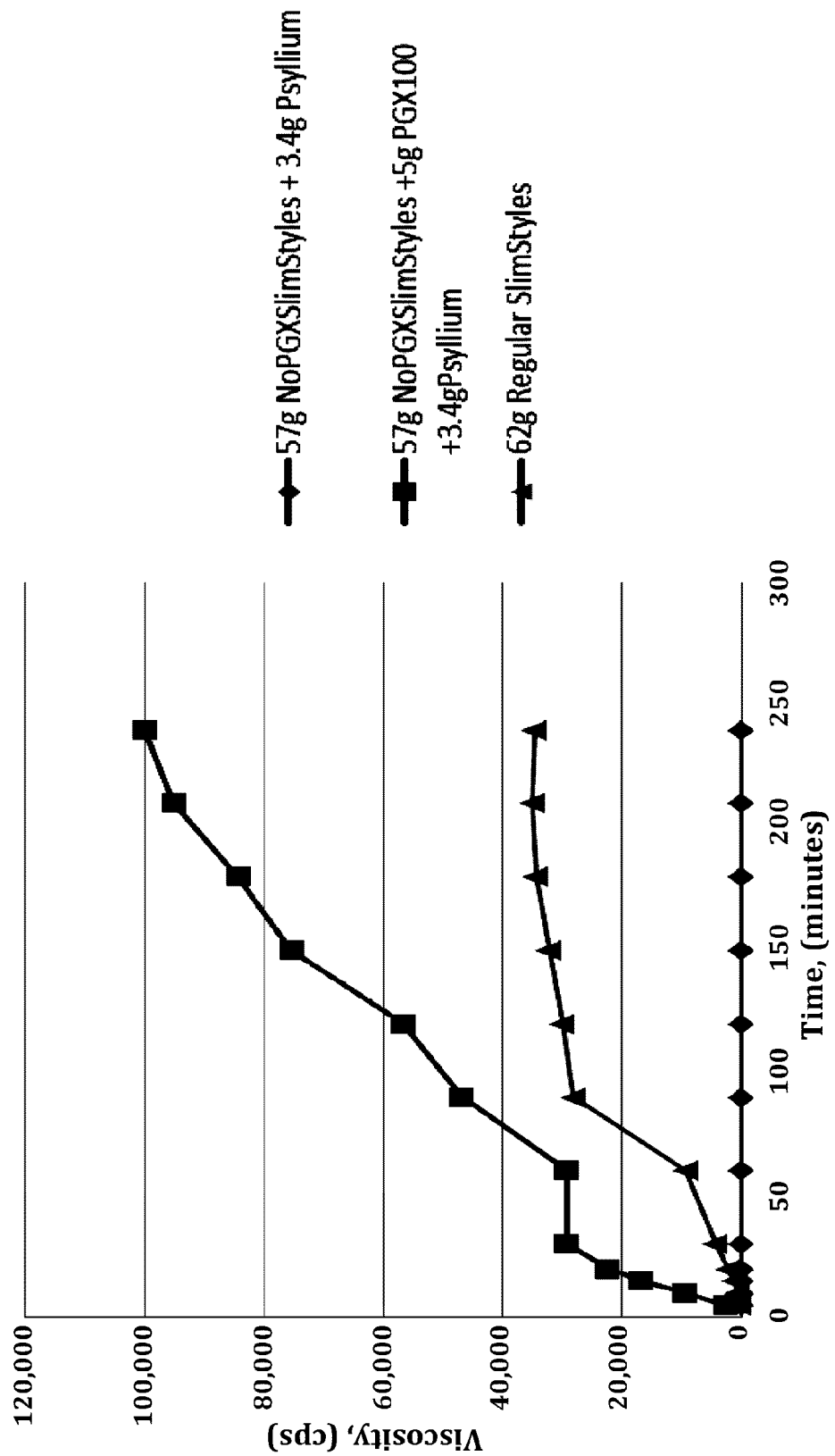
FIG. 11 graphically illustrates the viscosity profiles of representative compositions comprising PGX, psyllium and a combination of PGX and psyllium.

FIG. 11 graphically illustrates the viscosity profiles of the compositions in Samples 1-3 above. Referring to FIG. 11, Sample 2 comprising PGX and psyllium exhibits the highest viscosity profile. This demonstrates that adding psyllium to PGX 100 and SLIMSTYLES increases the viscosity profile, even when the PGX is granulated. As further shown in FIG. 11, Sample 1 has the lowest viscosity profile. This shows that adding psyllium to SLIMSTYLES has no effect on viscosity in the absence of PGX.

Experiment 3 clearly shows there is no viscosity development with psyllium alone, while regular SLIMSTYLES with PGX exhibits developing viscosity. However, having both PGX as the finer particle size 100 and psyllium added causes viscosity to rise far more than either SLIMSTYLES alone or psyllium alone. Without wishing to be bound by theory, the results appear to show an interaction between PGX and psyllium that causes an increase in viscosity that is several times greater than the viscosity of either alone. The result is totally unexpected in view of Experiments 1 and 2, as well as to someone skilled in the art.

Experiment 4

The following samples were prepared.
Sample 1: Non-granulated
Sample 2: Non-granulated
  57 g SLIMSTYLES base mix with no PGX
  2.5 g non-granulated PGX 100
  3.4 g psyllium
Sample 3: Non-granulated
  57 g SLIMSTYLES base mix with no PGX
  4 g non-granulated PGX 100
  2.72 g psyllium
Sample 4: Non-granulated
  57 g SLIMSTYLES base mix with no PGX
  4 g non-granulated PGX 100
  1.7 g psyllium
Sample 5: Non-granulated
  57 g SLIMSTYLES base mix with no PGX
  2.5 g non-granulated PGX 100
  1.7 g psyllium
Sample 6: 62 g regular SLIMSTYLES (57 g SLIMSTYLES base mix and 5 g PGX)

Each sample was mixed in 350 g deionized (DI) water and blended using a no. 3 spindle for 30 seconds at 4,000 RPM, followed by 30 seconds at 8,000 RPM. The samples were placed in a 25° C. water bath and viscosity readings were taken at the following time intervals: 5, 10, 15, 20, 30, 60, 90, 120, 150, 180, 210 and 240 minutes.

Figure 12:
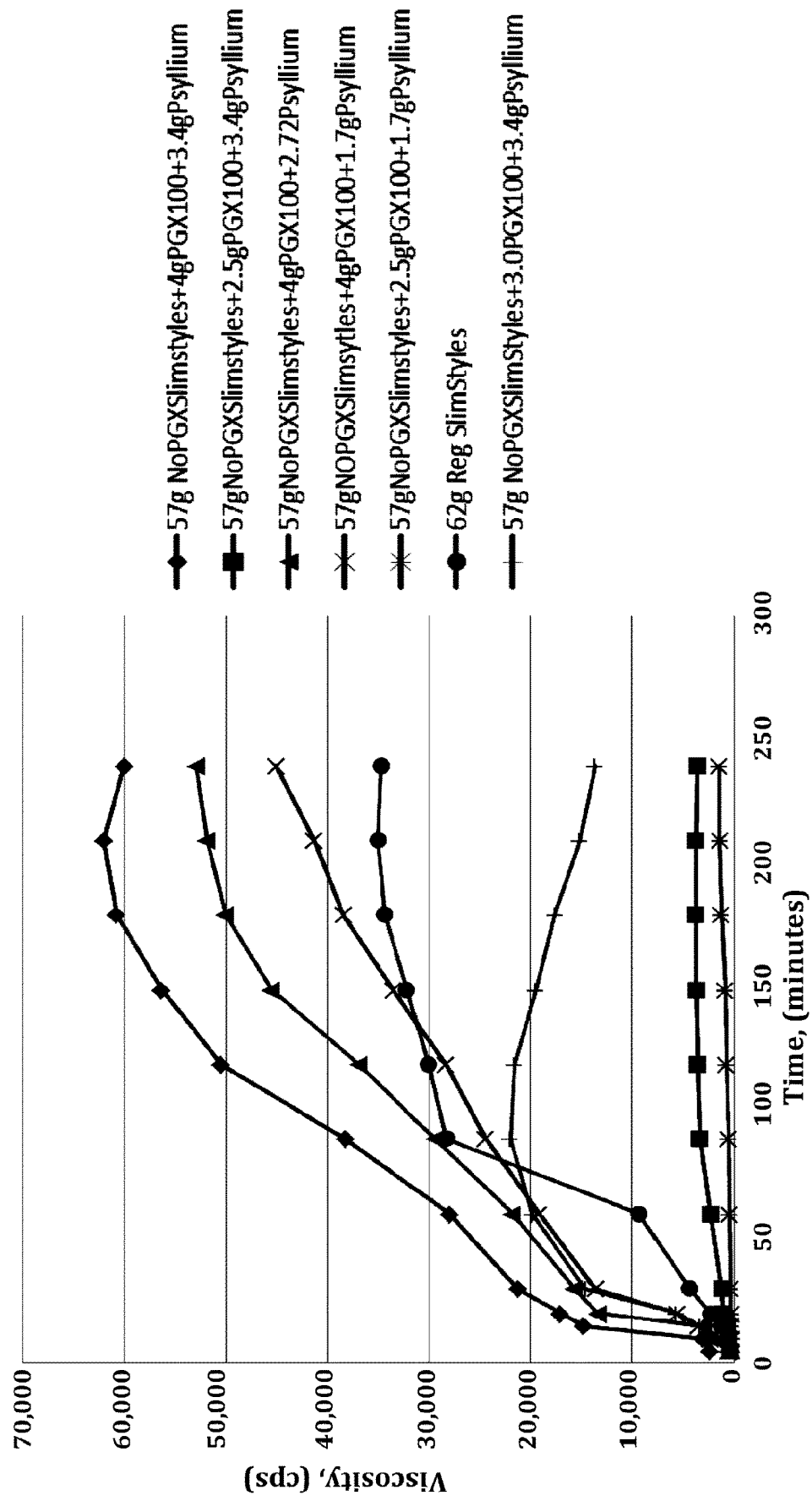
FIG. 12 graphically illustrates the viscosity profiles of representative compositions comprising PGX and psyllium.

FIG. 12 graphically illustrates the viscosity profiles of the compositions in Samples 1-6 above. Referring to FIG. 12, Sample 1 comprising 4 g PGX 100 and 3.4 g psyllium exhibited the highest viscosity profile, demonstrating that more PGX 100 increases the viscosity profile in SLIM-STYLES and more psyllium added to PGX 100 increases the viscosity profile in SLIMSTYLES. Lower PGX 100 and greater psyllium have a lower viscosity profile than higher PGX 100 and lower psyllium, confirming that PGX 100 is a greater thickening agent than psyllium.

Referring to FIG. 12, it is clear that the more PGX and psyllium present the greater the developing viscosity. Conversely the less of each cause a far lower viscosity. Even when there is a full amount of psyllium, if the PGX is low, the viscosity is low. The aim here was to see what ratio would mimic the SLIMSTYLES product while using less PGX and give a higher maximum viscosity within a 2 to 3-hour time frame (i.e., 120-180 minutes). Three sample compositions appear to meet these criteria: Sample 1, with 4 g PGX 100 and 3.4 g psyllium; Sample 3, with 4 g PGX 100 and 2.72 g psyllium; and Sample 4, with 4 g PGX and 1.7 g psyllium. Sample 5, with 2.5 g PGX 100 and 1.7 g psyllium started to develop viscosity and then at about 90 minutes started to lose viscosity. Without wishing to be bound by theory, it could be that whatever complex was formed started to break down.

Experiment 5

The following samples were prepared.
Sample 1: Non-granulated
    57 g SLIMSTYLES base mix with no PGX
    4 g non-granulated PGX 100
    3.4 g psyllium
Sample 2: Non-granulated
    57 g SLIMSTYLES base mix with no PGX
    4 g non-granulated PGX 100
    2.72 g psyllium
Sample 3: 61 g regular SLIMSTYLES (57 g SLIMSTYLES base mix and 4 g PGX)
Sample 4: Non-granulated
    57 g SLIMSTYLES base mix with no PGX
    3 g non-granulated PGX 100
    3.4 g psyllium
Sample 5: Non-granulated
    57 g SLIMSTYLES base mix with no PGX
    3.5 g non-granulated PGX 100
    3.4 g psyllium
Sample 6: Non-granulated
    57 g SLIMSTYLES base mix with no PGX
    3.5 g non-granulated PGX 100
    2.72 g psyllium Each sample was mixed in 350 g deionized (DI) water and blended using a no. 3 spindle for 30 seconds at 4,000 RPM, followed by 30 seconds at 8,000 RPM. The samples were placed in a 25° C. water bath and viscosity readings were taken at the following time intervals: 5, 10, 15, 20, 30, 60, 90, 120, 150, 180, 210 and 240 minutes.

Figure 13:
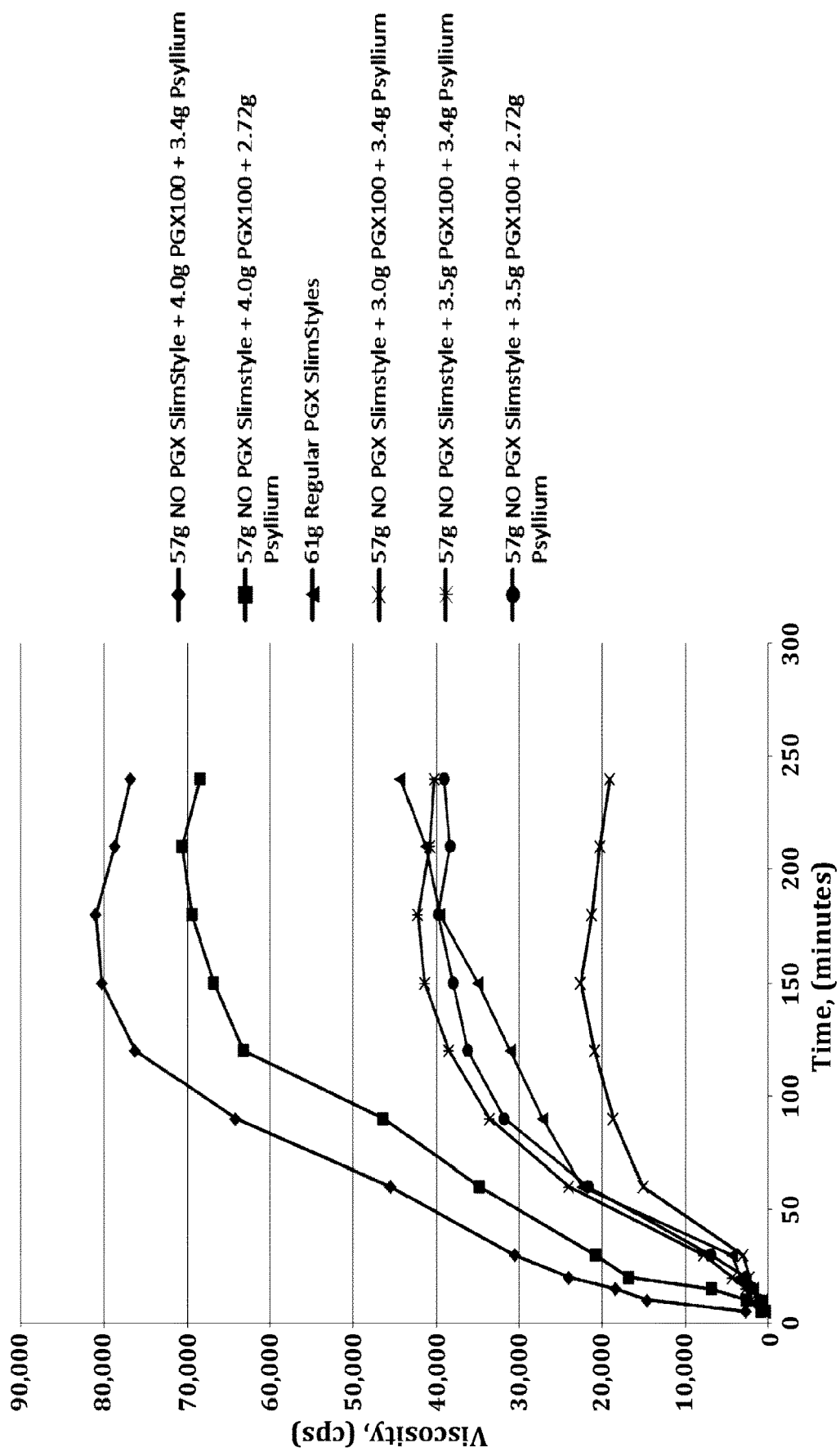
FIG. 13 graphically illustrates the viscosity profiles of representative compositions comprising PGX and psyllium.

FIG. 13 graphically illustrates the viscosity profiles of the compositions in Samples 1-6 above. Referring to FIG. 13, Sample 1 comprising 4 g PGX 100 and 3.4 g psyllium and Sample 2 comprising 4 g PGX 100 and 2.72 g psyllium, exhibited the highest viscosity profile.

Example 4

This example describes the viscosity profile of representative compositions comprising mixtures of PGX with psyllium in water and of konjac, sodium alginate, xanthan gum and psyllium in water.

Experiment 1

A sample containing 35.0094 g PGX 300 (Lot No. 862836; Inovobiologic Inc.) and 27.2074 g psyllium (Lot No. B901520; Inovobiologic Inc.) was mixed. Next, 62.24 g DI water was added and the sample was mixed for 2 minutes. The sample was dried at 108° C. until the Loss on Drying (LOD) was between 6-10%, or about 6.73%, then passed through a particle sieve having a mesh size of 20, 40, or 60 to produce a granulated mixture.

To prepare the sample for testing, 350.1 g DI water was added to a blender and the blender was started to create a vortex. Next, 5.023 g of the granulated mixture consisting of 3.309 g on 40 mesh, 1.506 g on 60 mesh, and 0.208 g through 60 mesh was sifted into the water vortex. The mixture was blended using a no. 3 spindle for 30 seconds at 4,000 RPM, followed by 30 seconds at 8,000 RPM. The sample was placed in a 25° C. water bath and viscosity readings were taken at time=10, 30, 60, 120, 180, and 240 minutes. The viscosity data in cps are shown in TABLE 10.

TABLE 10

| Time | Spindle | RPM | Viscosity |
| --- | --- | --- | --- |
| 10 | 3 | 50 | 730 |
| 30 | 3 | 10 | 4,360 |
| 60 | 3 | 5 | 9,540 |
| 120 | 3 | 1 | 46,740 |
| 180 | 3 | 1 | 81,780 |
| 240 | 3 | 1 | 88,410 |

As shown above, the sample reaches a maximum viscosity of about 88,410 cps at time=240 minutes.

Experiment 2

A sample containing 2.45 g konjac (Lot No. 13455; Inovobiologic Inc.), 0.5918 g xanthan gum (Lot No. 13967; Inovobiologic Inc.), 0.4602 g sodium alginate (Lot No. 13966, Inovobiologic Inc.) and 2.7207 g psyllium (Lot No. B901520; Inovobiologic Inc.) was mixed. To prepare the sample for testing, 350.1 g DI water was added to a blender and the blender was started to create a vortex. Next, 5.002 g of the mixture was sifted into the water vortex. The mixture was blended using a no. 3 spindle for 30 seconds at 4,000 RPM, followed by 30 seconds at 8,000 RPM. The sample was placed in a 25° C. water bath and viscosity readings were taken at time=10, 30, 60, 120, 180, and 240 minutes. The viscosity data in cps are shown in TABLE 11.

TABLE 11

| Time | Spindle | RPM | Viscosity |
| --- | --- | --- | --- |
| 10 | 3 | 50 | 1,030 |
| 30 | 3 | 10 | 4,330 |
| 60 | 3 | 2.5 | 22,730 |
| 120 | 3 | 1 | 59,780 |
| 180 | 3 | 1 | 45,920 |
| 240 | 3 | 1 | 37,230 |

As shown above, the sample reaches a maximum viscosity of about 59,780 cps at time=120 minutes.

Experiment 3

A sample containing 24.5 g konjac (Lot No. 13455; Inovobiologic Inc.), 5.918 g xanthan gum (Lot No. 13967; Inovobiologic Inc.), 4.602 g sodium alginate (Lot No. 13966, Inovobiologic Inc.) and 27.207 g psyllium (Lot No. B901520; Inovobiologic Inc.) was mixed. Next, 62.24 g DI water was added and the sample was mixed for 2 minutes. The sample was dried at 108° C. until the LOD was between 6-10%, or about 8.71%, then passed through a particle sieve having a mesh size of 20, 40, or 60 to produce a granulated mixture.

To prepare the sample for testing, 350.2 g DI water was added to a blender and the blender was started to create a vortex. Next, 5.002 g of the granulated mixture consisting of 3.516 g on 40 mesh and 1.486 g on 60 mesh was sifted into the water vortex. The mixture was blended using a no. 3 spindle for 30 seconds at 4,000 RPM, followed by 30 seconds at 8,000 RPM. The sample was placed in a 25° C. water bath and viscosity readings were taken at time=10, 30, 60, 120, 180, and 240 minutes. The viscosity data in cps are shown in TABLE 12.

TABLE 12

| Time | Spindle | RPM | Viscosity |
| --- | --- | --- | --- |
| 10 | 3 | 100 | 300 |
| 30 | 3 | 20 | 2,590 |
| 60 | 3 | 5 | 11,790 |
| 120 | 3 | 1 | 20,850 |
| 180 | 3 | 1 | 42,150 |
| 240 | 3 | 1 | 46,640 |

As shown above, the sample reaches a maximum viscosity of about 46,640 cps at time=240 minutes.

Experiment 4

A sample containing 3.505 g PGX 300 (Lot No. 862836; Inovobiologic Inc.) and 2.723 g psyllium (Lot No. B901520; Inovobiologic Inc.) was mixed. To prepare the sample for testing, 350.1 g DI water was added to a blender and the blender was started to create a vortex. Next, 5.004 g of the mixture was sifted into the water vortex. The mixture was blended using a no. 3 spindle for 30 seconds at 4,000 RPM, followed by 30 seconds at 8,000 RPM. The sample was placed in a 25° C. water bath and viscosity readings were taken at time=10, 30, 60, 120, 180, and 240 minutes. The viscosity data in cps are shown in TABLE 13.

TABLE 13

| Time | Spindle | RPM | Viscosity |
| --- | --- | --- | --- |
| 10 | 3 | 50 | 660 |
| 30 | 3 | 10 | 3,300 |
| 60 | 3 | 5 | 9,550 |
| 120 | 3 | 5 | 8,800 |
| 180 | 3 | 2.5 | 25,890 |
| 240 | 3 | 1 | 32,490 |

As shown above, the sample reaches a maximum viscosity of about 32,490 cps at time=240 minutes.

Experiment 5

A sample containing 5.002 g PGX 300 (Lot No. 862836; Inovobiologic Inc.) was used. To prepare the sample for testing, 350.1 g DI water was added to a blender and the blender was started to create a vortex. Next, 5.002 g of PGX 300 was sifted into the water vortex. The mixture was blended using a no. 3 spindle for 30 seconds at 4,000 RPM, followed by 30 seconds at 8,000 RPM. The sample was placed in a 25° C. water bath and viscosity readings were taken at time=10, 30, 60, 120, 180, and 240 minutes. The viscosity data in cps are shown in TABLE 14.

TABLE 14

| Time | Spindle | RPM | Viscosity |
| --- | --- | --- | --- |
| 10 | 3 | 20 | 1,810 |
| 30 | 3 | 10 | 4,770 |
| 60 | 3 | 5 | 10,000 |
| 120 | 3 | 5 | 12,300 |
| 180 | 3 | 2.5 | 22,730 |
| 240 | 3 | 2.5 | 25,160 |

As shown above, the sample reaches a maximum viscosity of about 25,160 cps at time=240 minutes.

Experiment 6

A sample containing 3.504 g PGX 100 (Lot No. 864781; Inovobiologic Inc.) and 2.72 g psyllium (Lot No. B901520; Inovobiologic Inc.) was mixed. To prepare the sample for testing, 350.1 g DI water was added to a blender and the blender was started to create a vortex. Next, 5.004 g of the mixture was sifted into the water vortex. The mixture was blended using a no. 3 spindle for 30 seconds at 4,000 RPM, followed by 30 seconds at 8,000 RPM. The sample was placed in a 25° C. water bath and viscosity readings were taken at time=10, 30, 60, 120, 180, and 240 minutes. The viscosity data in cps are shown in TABLE 15.

TABLE 15

| Time | Spindle | RPM | Viscosity |
| --- | --- | --- | --- |
| 10 | 3 | 50 | 850 |
| 30 | 3 | 10 | 3,650 |
| 60 | 3 | 5 | 11,840 |
| 120 | 3 | 5 | 13,150 |
| 180 | 3 | 2.5 | 25,340 |
| 240 | 3 | 1 | 35,990 |

As shown above, the sample reaches a maximum viscosity of about 35,990 cps at time=240 minutes.

Experiment 7

A sample containing 35.009 g PGX 100 (Lot No. 864781; Inovobiologic Inc.) and 27.2 g psyllium (Lot No. B901520; Inovobiologic Inc.) was mixed. Next, 62.2 g DI water was added and the sample was mixed for 2 minutes. The sample was dried at 108° C. until the LOD was between 6-10%, or about 8.19%, then passed through a particle sieve having mesh size 40 to produce a granulated mixture.

To prepare the sample for testing, 350.1 g DI water was added to a blender and the blender was started to create a vortex. Next, 5.001 g of the granulated mixture consisting of 0.189 g on 40 mesh and 4.812 g through 60 mesh was sifted into the water vortex. The mixture was blended using a no. 3 spindle for 30 seconds at 4,000 RPM, followed by 30 seconds at 8,000 RPM. The sample was placed in a 25° C. water bath and viscosity readings were taken at time=10, 30, 60, 120, 180, and 240 minutes. The viscosity data in cps are shown in TABLE 16.

TABLE 16

| Time | Spindle | RPM | Viscosity |
|---|---|---|---|
| 10 | 3 | 50 | 890 |
| 30 | 3 | 10 | 3,650 |
| 60 | 3 | 5 | 10,950 |
| 120 | 3 | 1 | 22,070 |
| 180 | 3 | 1 | 20,980 |
| 240 | 3 | 1 | 19,970 |

As shown above, the sample reaches a maximum viscosity of about 22,070 cps at time=120 minutes.

Experiment 8

A sample containing 24.5 g konjac (Lot No. 13455; Inovobiologic Inc.), 5.918 g xanthan gum (Lot No. 13967; Inovobiologic Inc.), 4.602 g sodium alginate (Lot No. 13966, Inovobiologic Inc.) and 27.207 g psyllium (Lot No. B901520; Inovobiologic Inc.) was mixed. Next, 62.2 g DI water was added and the sample was mixed for 2 minutes. The sample was dried at 108° C. until the LOD was between 6-10%, or about 8.71%, then passed through a particle sieve having a mesh size of 20, 40, or 60 to produce a granulated mixture.

To prepare the sample for testing, 350.2 g DI water was added to a blender and the blender was started to create a vortex. Next, 5.008 g of the granulated mixture consisting of 4.539 g on 60 mesh and 0.469 g on pan was sifted into the water vortex. The mixture was blended using a no. 3 spindle for 30 seconds at 4,000 RPM, followed by 30 seconds at 8,000 RPM. The sample was placed in a 25° C. water bath and viscosity readings were taken at time=10, 30, 60, 120, 180, and 240 minutes. The viscosity data in cps are shown in TABLE 17.

TABLE 17

| Time | Spindle | RPM | Viscosity |
|---|---|---|---|
| 10 | 3 | 50 | 970 |
| 30 | 3 | 20 | 3,080 |
| 60 | 3 | 5 | 10,650 |
| 120 | 3 | 1 | 62,680 |
| 180 | 3 | 1 | 58,570 |
| 240 | 3 | 1 | 68,300 |

As shown above, the sample reaches a maximum viscosity of about 68,300 cps at time=240 minutes.

Experiment 9

A sample containing 5.001 g PGX 100 (Lot No. 864781; Inovobiologic Inc.) was used. To prepare the sample for testing, 350.1 g DI water was added to a blender and the blender was started to create a vortex. Next, 5.001 g of the sample was sifted into the water vortex. The mixture was blended using a no. 3 spindle for 30 seconds at 4,000 RPM, followed by 30 seconds at 8,000 RPM. The sample was placed in a 25° C. water bath and viscosity readings were taken at time=10, 30, 60, 120, 180, and 240 minutes. The viscosity data in cps are shown in TABLE 18.

TABLE 18

| Time | Spindle | RPM | Viscosity |
|---|---|---|---|
| 10 | 3 | 20 | 2,130 |
| 30 | 3 | 10 | 4,960 |
| 60 | 3 | 5 | 9,660 |
| 120 | 3 | 2.5 | 20,100 |
| 180 | 3 | 1 | 41,350 |
| 240 | 3 | 1 | 49,220 |

As shown above, the sample reaches a maximum viscosity of about 49,220 cps at time=240 minutes.

Figure 14:
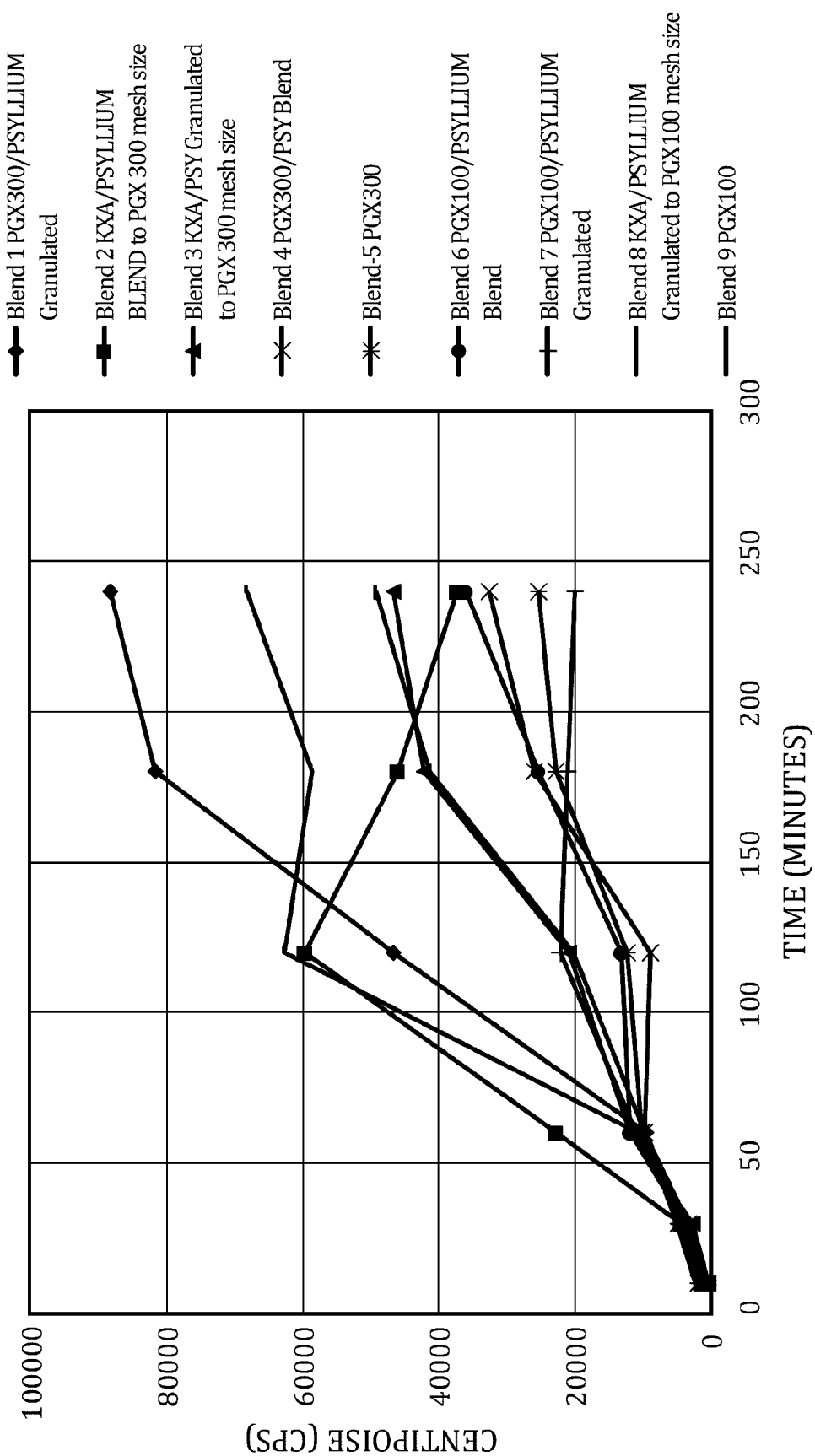
FIG. 14 graphically illustrates the viscosity profiles of representative compositions comprising PGX and psyllium.

FIG. 14 is a graphical representation of the viscosity data obtained from the sample compositions described in Experiments 1-9 above. The composition described in Experiment 1, or "Blend 1," contains a granulated mixture of PGX 300 and psyllium. The composition described in Experiment 8, or "Blend 8," contains a granulated mixture of konjac, xanthan gum, sodium alginate, and psyllium. Referring to FIG. 14, Blend 1 and Blend 8 exhibit a rapid increase in viscosity and reach a maximum viscosity at 240 minutes, with composition of Blend 8 reaching a higher viscosity than the composition of Blend 1.

The results are surprising because one skilled in the art would expect that a composition comprising granulated PGX that is mixed or blended with psyllium would exhibit about the same or less of an increase in viscosity compared to a composition comprising PGX and psyllium that are granulated together. Instead, the inventors unexpectedly discovered that compositions comprising PGX and psyllium granulated together exhibit a higher viscosity than compositions comprising granulated PGX mixed or blended with psyllium. The results suggest that PGX and psyllium when granulated together have a complimentary, possibly synergistic effect to produce a higher viscosity than PGX alone or a blended mixture of PGX and psyllium.

Example 5

This example describes an experiment where a composition comprising PGX and psyllium was administered to a group of subjects who were evaluated for changes in lipid profile, body weight and hemoglobin $A_1C$ (Hb$A_1$c).

The inventors have discovered that PGX and psyllium have a complimentary, possibly synergistic effect to produce a higher viscosity than PGX alone. Combinations of PGX and psyllium were evaluated and one was found to mirror the developing viscosity of PGX alone. This particular composition, comprising 3.75 grams PGX and 2.72 grams psyllium ("PGXPsyl"), was selected to test in a group of volunteers to evaluate against PGX over 4 weeks for lipid changes, weight changes, safety parameters and Hb$A_1$c.

Methods Ten subjects of either sex in an age range of 25-60 years consumed 5 g PGX or 3.75 g PGX blended with 2.72 g psyllium powder product twice a day for 30 days. The subjects were given a 3-week washout period and then repeated the 30-day study. The subjects were not taking any lipid lowering medication or natural health products for lipid lowering (e.g., Crestor®, statins, Lipitor®) during the course of the study.

Subjects submitted a blood sample and were tested for aspartate aminotransferase (AST), alanine transaminase (ALT), alkaline phosphatase (ALP), gamma-glutamyl transpeptidase (GGT), Na, K, creatinine, full lipid profile, glucose (fasting) and Hb$A_1$c after 12 hours fasting. The subjects had lipid levels (Total Cholesterol, LDL, HDL, non-HDL, LDL/HDL and triglycerides) tested after 12 hours of fasting and glucose, blood pressure, heart rate and weight measurements were also taken. Blood tests during the study were performed at +/−2 days.

Three to five days before starting to consume the study product, subjects had blood work done as described above and had lipids, glucose, weight, blood pressure (BP) and heart rate (HR) tested in a laboratory setting. Once it was confirmed that the subjects' results were within normal ranges, the subjects were allowed to continue with the study as follows:

Days 1-30: Subjects consumed 2×5 g of a first composition at breakfast and dinner. Subjects used supplied rating scale (100 mm VAS) to evaluate Bloating, Bowel Movement, Nausea, Satiety and Taste on day 1, 5, 10, 15, 20, 25 and 30, 3 hours after taking the product.

Days 7, 15, 22 and 30: Lipids and glucose were tested after a 12 hour fast. At day 30, subjects repeated the blood work panel and had lipids, glucose, weight, BP and HR re-tested.

Following a 3-week wash-out period, the above protocol was repeated with a second composition. Subjects consumed at least 500 ml water with each serving and returned any unused product.

The products used were (1) unlabeled sachets containing 5 g PGX and (2) unlabeled mixtures of 3.5 g PGX with 2.72 g psyllium milled to specification.

Discussion

Ten participants with an age range between 26 and 60, with a mean of 40.8 and a SD of 10.6 were enrolled in the study. Descriptive summaries were generated for all the measures of blood test results at day 1 and day 30, separately for the products. The outcomes were the changes in lipids, weight changes, safety parameters and $HbA_1c$ from baseline to the end of the study.

Over the course of the study, self-reported data of each participant's experience with the products at day 1, 5, 10, 15, 20, 25, 30 on satiety, taste, bloating, nausea and bowel movements were recorded. A p-value of 0.15 was used as a cut-off for statistical significance due to the small study size (n=10).

Lipid Change

Lipid lab results were computed and paired t-tests were used to detect the product difference. In both products, the significant decreases of cholesterol levels from day 1 to day 30 were observed in total cholesterol (TC), LDL, non-HDL, the ratio of total cholesterol and HDL. HDL remained relatively unchanged. However, PGX demonstrated a significantly larger reduction in cholesterol levels. Specifically, TC reduction: 0.8 in PGX and 0.4 in PGXPsyl (p-value=0.021); non-HDL reduction: 0.7 in PGX and 0.4 in PGXPsyl (p-value=0.088), ratio of TC/HDL reduction: 0.5 in PGX and 0.2 in PGXPsyl (p-value=0.042). Triglyceride levels showed an opposite change in PGX and PGXPsyl with an increase of 0.1 in PGX and a decrease of 0.1 on PGXPsyl (p-value=0.022). The data in TABLE 10, below, show a decrease in TC, LDL, HDL, non-HDL and LDL/HDL in subjects after consuming PGXPsyl for 30 days.

TABLE 10

Changes after 30 days on PGXPsyl

| ID | Name | Age | TC | LDL | HDL | non-HDL | LDL/HDL | TG |
|---|---|---|---|---|---|---|---|---|
| 1 | | 52 | −0.35 | −0.53 | −0.01 | −0.34 | −0.27 | 0.42 |
| 2 | | 45 | −0.24 | −0.22 | −0.04 | −0.20 | −0.07 | 0.04 |
| 3 | | 26 | 0.26 | 0.10 | 0.25 | 0.01 | −0.28 | −0.20 |
| 4 | | 34 | −0.60 | −0.77 | 0.03 | −0.63 | −0.30 | 0.31 |
| 5 | | 32 | −0.33 | −0.49 | −0.04 | −0.29 | −0.17 | 0.44 |
| 6 | | 60 | −1.16 | −0.96 | 0.01 | −1.17 | −0.63 | −0.46 |
| 7 | | 36 | −0.61 | −0.52 | −0.26 | −0.35 | 0.16 | 0.36 |
| 8 | | 45 | −0.45 | −0.48 | −0.03 | −0.42 | −0.32 | 0.12 |
| 9 | | 30 | 0.04 | 0.16 | −0.01 | 0.05 | 0.07 | −0.23 |
| 10 | | 48 | −0.67 | −0.45 | −0.22 | −0.45 | 0.01 | 0.00 |
| Average | | | −0.41 | −0.42 | −0.03 | −0.38 | −0.18 | 0.08 |

The cholesterol measures indicate that while PGXPsyl lowers blood cholesterol level compared to baseline blood cholesterol level measured at the start of this phase of the study, PGX performs better than PGXPsyl in lowering blood cholesterol levels.

Weight Management

PGX participants experienced a significant weight gain from day 1 to day 30. Correspondingly BMI elevated significantly from 24.8 to 25. Surprisingly, PGXPsyl showed the opposite changes in weight and accordingly, BMI decreased from day 1 to day 30; weight from 72 kg to 70.5 kg and BMI from 24.9 to 24.4. The product differences are significant in weight (p-value=0.008) and BMI (p-value=0.009).

This indicates that PGXPsyl has an unexpected and beneficial effect for weight loss and weight management as compared to PGX alone.

HA1C

From day 1 to day 30, $HbA_1c$ levels decreased by 0.1 unit in PGX but remained relatively unchanged in PGXPsyl.

This product difference is significant (p-value=0.089) and demonstrates that the PGXPsyl composition has an unexpected and beneficial role in maintaining blood sugar levels as compared to PGX alone.

Safety Measures

There were no product differences for all of the indexes of these test results.

Participants' Experience with Compositions

The longitudinal data were analyzed using nonparametric regression splines for trends and generalized estimating equations models to identify the composition differences.

Over the 30-day window of each product use, the study participants' experiences with the compositions was summarized by the diary scales (1-10) in satiety, taste, bloating, nausea and bowel movements. Participants were asked to circle the number most closely resembling how they felt.

There were no temporal trend differences in satiety (p-value=0.749), taste (p-value=0.282), bloating (p-value=0.540), nausea (p-value=0.977). However, bowel movement demonstrates elevated score levels associated with PGXPsyl use (p-value=0.001). However, the PGXPsyl pattern shows that after a week or so, the score level stabilized. Exemplary data are shown below.

| DAY 1 Satiety #1 | | | | | | | | | |
|---|---|---|---|---|---|---|---|---|---|
| 10 Full | 9 (3) | 8 (1) | 7 (1) | 6 | 5 (1) | 4 | 3 | 2 (1) | 1 Empty |

-continued

| | | | | | | | | | |
|---|---|---|---|---|---|---|---|---|---|
| Satiety #2 | | | | | | | | | |
| 10 (1) Full | 9 | 8 (1) | 7 (1) | 6 (1) | 5 (2) | 4 | 3 | 2 | 1 Empty |
| Satiety #3 | | | | | | | | | |
| 10 Full | 9 (1) | 8 (3) | 7 | 6 (1) | 5 | 4 | 3 (1) | 2 | 1 Empty |
| Taste #1 | | | | | | | | | |
| 10 Great (1) | 9 (1) | 8 | 7 (2) | 6 (1) | 5 (1) | 4 | 3 | 2 (1) | 1 can't eat |
| Taste #2 | | | | | | | | | |
| 10 Great | 9 | 8 | 7 | 6 (1) | 5 (3) | 4 | 3 | 2 (1) | 1 can't eat |
| Taste #3 | | | | | | | | | |
| 10 Great | 9 | 8 | 7 | 6 | 5 (1) | 4 (3) | 3 | 2 (1) | 1 can't eat |
| Bloating #1 | | | | | | | | | |
| 10 Extreme | 9 | 8 | 7 (2) | 6 | 5 (1) | 4 | 3 | 2 (2) | 1 None (2) |
| Bloating #2 | | | | | | | | | |
| 10 Extreme | 9 | 8 (1) | 7 (1) | 6 | 5 (1) | 4 | 3 | 2 (3) | 1 None |
| Bloating #3 | | | | | | | | | |
| 10 Extreme | 9 | 8 (1) | 7 | 6 (1) | 5 (1) | 4 (1) | 3 (1) | 2 | 1 (1) None |
| Bowel Movement #1 | | | | | | | | | |
| 10 (1) Diarrhea | 9 | 8 | 7 (1) | 6 | 5 (4) Normal | 4 (1) | 3 | 2 | 1 Constipated |
| Bowel Movement #2 | | | | | | | | | |
| 10 Diarrhea | 9 | 8 (2) | 7 (1) | 6 | 5 (3) Normal | 4 | 3 | 2 | 1 Constipated |
| Bowel Movement #3 | | | | | | | | | |
| 10 Diarrhea | 9 | 8 (1) | 7 (1) | 6 | 5 Normal | 4 (4) | 3 | 2 | 1 Constipated |
| DAY 2 | | | | | | | | | |
| Satiety #1 | | | | | | | | | |
| 10 Full | 9 (2) | 8 (2) | 7 (2) | 6 (1) | 5 | 4 | 3 | 2 | 1 Empty |
| Satiety #2 | | | | | | | | | |
| 10 (1) Full | 1 | 8 | 7 (2) | 6 (1) | 5 (2) | 4 | 3 | 2 | 1 Empty |
| Satiety #3 | | | | | | | | | |
| 10 Full | 9 (2) | 8 (1) | 7 (1) | 6 | 5 | 4 (1) | 3 (1) | 2 | 1 Empty |
| Taste #1 | | | | | | | | | |
| 10 (1) Great | 9 | 8 (1) | 7 (1) | 6 (2) | 5 (1) | 4 | 3 | 2 (1) | 1 can't eat |
| Taste #2 | | | | | | | | | |
| 10 Great | 9 | 8 | 7 | 6 (1) | 5 (4) | 4 | 3 | 2 (1) | 1 can't eat |
| Taste #3 | | | | | | | | | |
| 10 Great | 9 | 8 | 7 (1) | 6 (1) | 5 (2) | 4 (1) | 3 | 2 (1) | 1 can't eat |
| Bloating #1 | | | | | | | | | |
| 10 Extreme | 9 | 8 | 7 | 6 (1) | 5 (1) | 4 | 3 | 2 (2) | 1 (2) None |
| Bloating #2 | | | | | | | | | |
| 10 Extreme | 9 | 8 | 7 (1) | 6 | 5 (2) | 4 | 3 (1) | 2 (1) | 1 (1) None |

-continued

| | | | | | | | | | |
|---|---|---|---|---|---|---|---|---|---|
| Bloating #3 | | | | | | | | | |
| 10 Extreme | 9 | 8 (1) | 7 | 6 (1) | 5 (1) | 4 | 3 (2) | 2 (1) | 1 None |
| Bowel Movement #1 | | | | | | | | | |
| 10 Diarrhea | 9 (1) | 8 | 7 (1) | 6 (2) | 5 (1) Normal | 4 (1) | 3 (1) | 2 | 1 Constipated |
| Bowel Movement #2 | | | | | | | | | |
| 10 Diarrhea | 9 | 8 (1) | 7 (1) | 6 | 5 (3) Normal | 4 (1) | 3 | 2 | 1 Constipated |
| Bowel Movement #3 | | | | | | | | | |
| 10 Diarrhea | 9 | 8 | 7 | 6 (2) | 5 (3) Normal | 4 | 3 (1) | 2 | 1 Constipated |
| DAY 3 | | | | | | | | | |
| Satiety #1 | | | | | | | | | |
| 10 (1) Full | 9 (1) | 8 (1) | 7 (1) | 6 (1) | 5 | 4 | 3 | 2 (1) | 1 Empty |
| Satiety #2 | | | | | | | | | |
| 10 (1) Full | 9 | 8 | 7 (2) | 6 (1) | 5 (2) | 4 | 3 | 2 | 1 Empty |
| Satiety #3 | | | | | | | | | |
| 10 Full | 9 (1) | 8 (1) | 7 (2) | 6 | 5 | 4 (1) | 3 (1) | 2 | 1 Empty |
| Taste #1 | | | | | | | | | |
| 10 (1) Great | 9 | 8 (1) | 7 | 6 (1) | 5 (2) | 4 | 3 | 2 (1) | 1 can't eat |
| Taste #2 | | | | | | | | | |
| 10 Great | 9 | 8 | 7 (1) | 6 | 5 (4) | 4 | 3 | 2 (1) | 1 can't eat |
| Taste #3 | | | | | | | | | |
| 10 Great | 9 | 8 | 7 (1) | 6 | 5 (1) | 4 (1) | 3 (1) | 2 (2) | 1 can't eat |
| Bloating #1 | | | | | | | | | |
| 10 Extreme | 9 | 8 | 7 | 6 | 5 (3) | 4 (1) | 3 | 2 | 1 (2) None |
| Bloating #2 | | | | | | | | | |
| 10 Extreme | 9 | 8 | 7 (1) | 6 | 5 (2) | 4 | 3 (1) | 2 (1) | 1 (1) None |
| Bloating #3 | | | | | | | | | |
| 10 Extreme | 9 | 8 | 7 | 6 (1) | 5 (2) | 4 | 3 (1) | 2 (2) | 1 None |
| Bowel Movement #1 | | | | | | | | | |
| 10 Diarrhea | 9 1 | 8 | 7 (2) | 6 (2) | 5 (1) Normal | 4 (1) | 3 | 2 | 1 Constipated |
| Bowel Movement #2 | | | | | | | | | |
| 10 Diarrhea | 9 1 | 8 | 7 (1) | 6 (2) | 5 (3) Normal | 4 | 3 | 2 | 1 Constipated |
| Bowel Movement #3 | | | | | | | | | |
| 10 Diarrhea | 9 1 | 8 | 7 (1) | 6 | 5 (3) Normal | 4 | 3 (1) | 2 | 1 Constipated |
| DAY 4 | | | | | | | | | |
| Satiety #1 | | | | | | | | | |
| 10 (1) Full | 9 (1) | 8 (3) | 7 | 6 | 5 | 4 (1) | 3 | 2 | 1 Empty |
| Satiety #2 | | | | | | | | | |
| 10 (1) Full | 9 | 8 | 7 (2) | 6 (2) | 5 (1) | 4 | 3 | 2 | 1 Empty |
| Satiety #3 | | | | | | | | | |
| 10 Full | 9 | 8 (2) | 7 (3) | 6 | 5 (1) | 4 | 3 | 2 | 1 Empty |

-continued

| | | | | Taste #1 | | | | | |
|---|---|---|---|---|---|---|---|---|---|
| 10 (1) Great | 9 | 8 | 7 (2) | 6 (1) | 5 (1) | 4 | 3 | 2 | 1) 1 can't eat |

| | | | | Taste #2 | | | | | |
|---|---|---|---|---|---|---|---|---|---|
| 10 Great | 9 | 8 | 7 | 6 (1) | 5 (4) | 4 | 3 | 2 | 1) 1 can't eat |

| | | | | Taste #3 | | | | | |
|---|---|---|---|---|---|---|---|---|---|
| 10 Great | 9 | 8 | 7 | 6 | 5 (2) | 4 (1) | 3 (2) | 2 | 1) 1 can't eat |

| | | | | Bloating #1 | | | | | |
|---|---|---|---|---|---|---|---|---|---|
| 10 Extreme | 9 | 8 | 7 | 6 (1) | 5 (1) | 4 (1) | 3 | 2 (1) | 1 (2) None |

| | | | | Bloating #2 | | | | | |
|---|---|---|---|---|---|---|---|---|---|
| 10 Extreme | 9 | 8 (1) | 7 | 6 | 5 (1) | 4 | 3 (2) | 2 (1) | 1 (1) None |

| | | | | Bloating #3 | | | | | |
|---|---|---|---|---|---|---|---|---|---|
| 10 Extreme | 9 | 8 | 7 | 6 | 5 | 4 | 3 | 2 | 1 None |

| | | | | Bowel Movement #1 | | | | | |
|---|---|---|---|---|---|---|---|---|---|
| 10 Diarrhea | 9 | 8 | 7 (2) | 6 (2) | 5 (2) Normal | 4 | 3 | 2 | 1 Constipated |

| | | | | Bowel Movement #2 | | | | | |
|---|---|---|---|---|---|---|---|---|---|
| 10 Diarrhea | 9 | 8 | 7 (1) | 6 | 5 (2) Normal | 4 | 3 | 2 | 1 Constipated |

| | | | | Bowel Movement #3 | | | | | |
|---|---|---|---|---|---|---|---|---|---|
| 10 Diarrhea | 9 | 8 | 7 (1) 6 | 6 (1) | 5 (2) Normal | 4 (1) | 3 | 2 (1) | 1 Constipated |

DAY 5

| | | | | Satiety #1 | | | | | |
|---|---|---|---|---|---|---|---|---|---|
| 10 (1) Full | 1 (1) | 8 | 7 (2) | 6 (1) | 5 | 4 (1) | 3 | 2 | 1 Empty |

| | | | | Satiety #2 | | | | | |
|---|---|---|---|---|---|---|---|---|---|
| 10 (1) Full | | 8 | 7 (2) | 6 (2) | 5 (1) | 4 | 3 | 2 | 1 Empty |

| | | | | Satiety #3 | | | | | |
|---|---|---|---|---|---|---|---|---|---|
| 10 (1) Full | | 8 (2) | 7 (1) | 6 (1) | 5 | 4 (1) | 3 | 2 | 1 Empty |

| | | | | Taste #1 | | | | | |
|---|---|---|---|---|---|---|---|---|---|
| 10 (1) Great | 9 | 8 | 7 (1) | 6 (1) | 5 (2) | 4 | 3 | 2 (1) | 1 can't eat |

| | | | | Taste #2 | | | | | |
|---|---|---|---|---|---|---|---|---|---|
| 10 Great | 9 | 8 (1) | 7 | 6 | 5 (4) | 4 | 3 | 2 (1) | 1 can't eat |

| | | | | Taste #3 | | | | | |
|---|---|---|---|---|---|---|---|---|---|
| 10 Great | 9 | 8 | 7 | 6 (1) | 5 (1) | 4 (1) | 3 (2) | 2 (1) | 1 can't eat |

| | | | | Bloating #1 | | | | | |
|---|---|---|---|---|---|---|---|---|---|
| 10 Extreme | 9 | 8 | 7 (1) | 6 (1) | 5 | 4 | 3 (1) | 2 (2) | 1 (1) None |

| | | | | Bloating #2 | | | | | |
|---|---|---|---|---|---|---|---|---|---|
| 10 Extreme | 9 | 8 (1) | 7 | 6 | 5 (1) | 4 (1) | 3 | 2 (3) | 1 None |

| | | | | Bloating #3 | | | | | |
|---|---|---|---|---|---|---|---|---|---|
| 10 Extreme | 9 | 8 | 7 | 6 | 5 (1) | 4 | 3 (3) | 2 | 1 (2) None |

| | | | | Bowel Movement #1 | | | | | |
|---|---|---|---|---|---|---|---|---|---|
| 10 Diarrhea | 9 | 8 (1) | 7 (2) | 6 | 5 (3) Normal | 4 | 3 | 2 | 1 Constipated |

-continued

| | | | | | | | | | |
|---|---|---|---|---|---|---|---|---|---|
| | Bowel Movement #2 |||||||||
| 10 Diarrhea | 9 | 8 (1) | 7 | 6 | 5 (4) Normal | 4 (1) | 3 | 2 | 1 Constipated |
| | Bowel Movement #3 |||||||||
| 10 Diarrhea | 9 | 8 | 7 (1) | 6 | 5 (3) Normal | 4 | 3 (2) | 2 | 1 Constipated |
| | DAY 6 Satiety #1 |||||||||
| 10 Full | 9 | 8 (1) | 7 (3) | 6 (1) | 5 | 4 (1) | 3 | 2 | 1 Empty |
| | Satiety #2 |||||||||
| 10 (1) Full | 9 | 8 | 7 (2) | 6 (1) | 5 (2) | 4 | 3 | 2 | 1 Empty |
| | Satiety #3 |||||||||
| 10 Full | 9 | 8 (2) | 7 (2) | 6 (1) | 5 (1) | 4 | 3 | 2 | 1 Empty |
| | Taste #1 |||||||||
| 10 (1) Great | 9 | 8 | 7 | 6 (1) | 5 (2) | 4 (1) | 3 | 2 (1) | 1 can't eat |
| | Taste #2 |||||||||
| 10 Great | 9 | 8 (1) | 7 | 6 | 5 (3) | 4 (1) | 3 | 2 (1) | 1 can't eat |
| | Taste #3 |||||||||
| 10 Great | 9 | 8 | 7 | 6 | 5 (2) | 4 (1) | 3 (2) | 2 (1) | 1 can't eat |
| | Bloating #1 |||||||||
| 10 Extreme | 9 | 8 | 7 (1) | 6 | 5 (1) | 4 | 3 (2) | 2 | 1 (2) None |
| | Bloating #2 |||||||||
| 10 Extreme | 9 | 8 | 7 (1) | 6 | 5 (1) | 4 (1) | 3 | 2 (3) | 1 None |
| | Bloating #3 |||||||||
| 10 Extreme | 9 | 8 | 7 | 6 (1) | 5 (1) | 4 | 3 (1) | 2 (1) | 1 (2) None |
| | Bowel Movement #1 |||||||||
| 10 Diarrhea | 9 | 8 | 7 (1) | 6 (1) | 5 (4) Normal | 4 | 3 | 2 | 1 Constipated |
| | Bowel Movement #2 |||||||||
| 10 Diarrhea | 9 | 8 (2) | 7 | 6 | 5 (4) Normal | 4 | 3 | 2 | 1 Constipated |
| | Bowel Movement #3 |||||||||
| 10 Diarrhea | 9 | 8 (1) | 7 | 6 (1) | 5 (4) Normal | 4 | 3 | 2 | 1 Constipated |
| | DAY 7 Satiety #1 |||||||||
| 10 (1) Full | 1 (1) | 8 | 7 (3) | 6 | 5 | 4 (1) | 3 | 2 | 1 Empty |
| | Satiety #2 |||||||||
| 10 Full | 1 (1) | 8 | 7 (2) | 6 (2) | 5 (1) | 4 | 3 | 2 | 1 Empty |
| | Satiety #3 |||||||||
| 10 Full | 1 (1) | 8 (2) | 7 (1) | 6 | 5 | 4 (2) | 3 | 2 | 1 Empty |
| | Taste #1 |||||||||
| 10 (1) Great | 9 | 8 | 7 | 6 (2) | 5 (2) | 4 | 3 | 2 (1) | 1 can't eat |
| | Taste #2 |||||||||
| 10 Great | 9 | 8 (1) | 7 | 6 (1) | 5 (2) | 4 (1) | 3 | 2 (1) | 1 can't eat |

-continued

| | | | | | Taste #3 | | | | |
|---|---|---|---|---|---|---|---|---|---|
| 10 Great | 9 | 8 | 7 | 6 | 5 (3) | 4 | 3 (2) | 2 (1) | 1 can't eat |

| | | | | | Bloating #1 | | | | |
|---|---|---|---|---|---|---|---|---|---|
| 10 Extreme | 9 | 8 | 7 (1) | 6 | 5 (2) | 4 | 3 (2) | 2 (1) | 1 None |

| | | | | | Bloating #2 | | | | |
|---|---|---|---|---|---|---|---|---|---|
| 10 Extreme | 9 | 8 | 7 (1) | 6 | 5 (1) | 4 (1) | 3 | 2 (2) | 1 (1) None |

| | | | | | Bloating #3 | | | | |
|---|---|---|---|---|---|---|---|---|---|
| 10 Extreme | 9 | 8 | 7 | 6 (1) | 5 | 4 | 3 (2) | 2 (2) | 1 (1) None |

| | | | | | Bowel Movement #1 | | | | |
|---|---|---|---|---|---|---|---|---|---|
| 10 Diarrhea | 9 | 8 | 7 | 6 | 5 (3) Normal | 4 (2) | 3 | 2 (1) | 1 Constipated |

| | | | | | Bowel Movement #2 | | | | |
|---|---|---|---|---|---|---|---|---|---|
| 10 Diarrhea | 9 | 8 (1) | 7 (1) | 6 | 5 (4) Normal | 4 | 3 | 2 | 1 Constipated |

| | | | | | Bowel Movement #3 | | | | |
|---|---|---|---|---|---|---|---|---|---|
| 10 Diarrhea | 9 | 8 | 7 | 6 | 5 (3) Normal | 4 (3) | 3 | 2 | 1 Constipated |

The results demonstrate that an exemplary composition comprising PGX and psyllium facilitates weight loss, weight management, lowering blood cholesterol levels and lowering blood glucose levels compared to a composition comprising PGX alone.

While illustrative embodiments have been illustrated and described, it will be appreciated that various changes can be made therein without departing from the spirit and scope of the invention.

The invention claimed is:

1. A polysaccharide dietary fiber composition comprising (i) from about 40% to about 80% (w/w) of a granulated fiber composition comprising glucomannan, xanthan gum, and alginate; and (ii) from about 10% to about 60% (w/w) psyllium;
wherein the initial viscosity in water is 200 to 1000 centipoise (cps) and the viscosity after 30 minutes is 3,000 to 5,000 or more cps.

2. The polysaccharide dietary fiber composition of claim 1 comprising from about 50% to about 60% (w/w) of the granulated fiber composition and from about 40% to about 50% (w/w) psyllium.

3. The polysaccharide dietary fiber composition of claim 1, wherein the granulated fiber composition comprises from about 50% to about 90% (w/w) glucomannan, from about 5% to about 20% (w/w) xanthan gum, and from about 5% to about 30% (w/w) alginate.

4. The polysaccharide dietary fiber composition of claim 1, wherein the granulated fiber composition comprises from about 60% to about 80% (w/w) glucomannan, from about 10% to about 20% (w/w) xanthan gum, and from about 10% to about 20% (w/w) alginate.

5. The polysaccharide dietary fiber composition of claim 1, wherein the granulated fiber composition and psyllium are granulated together.

6. The polysaccharide dietary granulated fiber composition of claim 1, further comprising at least one lipid or blend thereof, wherein the lipid or blend thereof comprises at least 20% (w/w) of the total granulated fiber composition.

7. The polysaccharide dietary fiber composition of claim 1, wherein the dietary granulated fiber composition is contained in a soft gel capsule, compounded into a tablet, or formulated into a powder.

8. A medical food product for promoting satiety, promoting weight loss, lowering blood cholesterol levels or lowering blood glucose levels in a mammal comprising a polysaccharide dietary granulated fiber composition comprising a highly viscous fiber complex comprising (i) from about 40% to about 80% (w/w) of a granulated fiber composition comprising glucomannan, xanthan gum, and alginate; and (ii) from about 10% to about 60% (w/w) psyllium;
wherein the initial viscosity is 200 to 1,000 cps and the viscosity after 30 min is 3,000 to 5,000 or more cps.

9. The medical food product of claim 8, wherein the polysaccharide dietary granulated fiber composition comprises from about 50% to about 90% (w/w) glucomannan, from about 5% to about 20% (w/w) xanthan gum, and from about 5% to about 30% (w/w) alginate.

10. The medical food product of claim 8, wherein the highly viscous polysaccharide dietary granulated fiber composition and psyllium are granulated together.

11. The medical food product of claim 8, wherein the food product is a dietary supplement or a meal replacement product.

12. The medical food product of claim 8, wherein the medical food product is compounded to provide daily dose of from about 5 g to about 20 g of the highly viscous polysaccharide dietary granulated fiber composition.

* * * * *